(12) United States Patent
Aragones et al.

(10) Patent No.: US 11,094,410 B2
(45) Date of Patent: Aug. 17, 2021

(54) METHOD AND SYSTEM FOR AUTOMATED PERSONAL TRAINING

(71) Applicant: NIKE, Inc., Beaverton, OR (US)

(72) Inventors: Teresa Aragones, Portland, OR (US); Byron G. Merritt, Portland, OR (US); Christina S. Self, Portland, OR (US); Willoughby H. Walling, Portland, OR (US); Xavier Jacob, London (GB); Geoff Northcott, London (GB); Robert Thomsen, London (GB)

(73) Assignee: NIKE, Inc., Beaverton, OR (US)

( * ) Notice: Subject to any disclaimer, the term of this patent is extended or adjusted under 35 U.S.C. 154(b) by 0 days.

(21) Appl. No.: 16/741,492

(22) Filed: Jan. 13, 2020

(65) Prior Publication Data

US 2020/0147454 A1 May 14, 2020

Related U.S. Application Data

(63) Continuation of application No. 15/174,665, filed on Jun. 6, 2016, now Pat. No. 10,583,328, which is a
(Continued)

(51) Int. Cl.
*A63B 24/00* (2006.01)
*A63B 22/00* (2006.01)
(Continued)

(52) U.S. Cl.
CPC ........... *G16H 20/30* (2018.01); *A43B 3/0005* (2013.01); *A63B 22/00* (2013.01); *A63B 22/001* (2013.01);
(Continued)

(58) Field of Classification Search
CPC .... A63B 2024/0078; A63B 2024/0081; A63B 24/0074; A63B 24/0084; A63B 24/00;
(Continued)

(56) References Cited

U.S. PATENT DOCUMENTS 3,145,484 A 8/1964 Bayley
4,938,476 A 7/1990 Brunelle et al.
(Continued)

FOREIGN PATENT DOCUMENTS

CN 1415271 A 5/2003
CN 1723847 A 1/2006
(Continued)

OTHER PUBLICATIONS

Jun. 27, 2013 (WO)—International Preliminary Report on Patentability—App. No. PCT/US2011/064711.
(Continued)

*Primary Examiner* — Robert J Utama
(74) *Attorney, Agent, or Firm* — Banner & Witcoff, Ltd.

(57) ABSTRACT

Example embodiments may relate to a system, method, apparatus, and computer readable media configured for monitoring a user performing an exercise and generating a avatar of the user and a virtual shadow, wherein the virtual shadow illustrates proper form of the exercise. The example embodiments may further be configured for determining an amount of overlap between the virtual avatar and the virtual shadow, and generating a feedback score based on the amount of overlap.

20 Claims, 20 Drawing Sheets

Related U.S. Application Data continuation of application No. 13/290,478, filed on Nov. 7, 2011, now Pat. No. 9,358,426.

(60) Provisional application No. 61/433,792, filed on Jan. 18, 2011, provisional application No. 61/432,472, filed on Jan. 13, 2011, provisional application No. 61/422,511, filed on Dec. 13, 2010, provisional application No. 61/417,102, filed on Nov. 24, 2010, provisional application No. 61/410,777, filed on Nov. 5, 2010.

(51) Int. Cl.
| | | |
|---|---|---|
| *G09B 19/00* | (2006.01) | |
| *G16H 20/30* | (2018.01) | |
| *G16H 50/30* | (2018.01) | |
| *G16H 50/70* | (2018.01) | |
| *A43B 3/00* | (2006.01) | |
| *A63B 71/06* | (2006.01) | |
| *G16H 40/67* | (2018.01) | |

(52) U.S. Cl.
CPC .......... *A63B 24/00* (2013.01); *A63B 24/0003* (2013.01); *A63B 24/0006* (2013.01); *A63B 24/0062* (2013.01); *A63B 24/0075* (2013.01); *A63B 24/0084* (2013.01); *A63B 71/0622* (2013.01); *G09B 19/0038* (2013.01); *G16H 50/30* (2018.01); *G16H 50/70* (2018.01); *A63B 2024/0009* (2013.01); *A63B 2024/0012* (2013.01); *A63B 2024/0015* (2013.01); *A63B 2071/065* (2013.01); *A63B 2220/05* (2013.01); *A63B 2220/12* (2013.01); *A63B 2220/40* (2013.01); *A63B 2220/72* (2013.01); *A63B 2220/80* (2013.01); *A63B 2230/06* (2013.01); *A63B 2230/50* (2013.01); *G16H 40/67* (2018.01)

(58) Field of Classification Search
CPC ............ A63B 24/0003; A63B 24/0006; A63B 24/009; A63B 2220/806; A63B 24/0021
See application file for complete search history.

(56) References Cited

U.S. PATENT DOCUMENTS

| | | |
|---|---|---|
| 5,184,295 A | 2/1993 | Mann |
| 5,277,197 A | 1/1994 | Church et al. |
| 5,288,078 A | 2/1994 | Capper et al. |
| 5,335,188 A | 8/1994 | Brisson |
| 5,354,317 A | 10/1994 | Alt |
| 5,375,610 A | 12/1994 | LaCourse et al. |
| 5,511,789 A | 4/1996 | Nakamura |
| 5,524,637 A | 6/1996 | Erickson |
| 5,527,239 A | 6/1996 | Abbondanza |
| 5,598,849 A | 2/1997 | Browne |
| 5,655,316 A | 8/1997 | Huang |
| 5,667,459 A | 9/1997 | Su |
| 5,688,137 A | 11/1997 | Bustance |
| 5,791,351 A | 8/1998 | Curchod |
| 5,826,578 A | 10/1998 | Curchod |
| 5,836,770 A | 11/1998 | Powers |
| 5,846,086 A | 12/1998 | Bizzi et al. |
| 5,851,193 A | 12/1998 | Arikka et al. |
| 5,904,484 A | 5/1999 | Burns |
| 5,913,727 A | 6/1999 | Ahdoot |
| 5,919,149 A | 7/1999 | Allum |
| 5,938,690 A | 8/1999 | Law et al. |
| 5,955,957 A | 9/1999 | Calabrese et al. |
| 5,976,083 A | 11/1999 | Richardson et al. |
| 6,126,449 A | 10/2000 | Burns |
| 6,308,565 B1 | 10/2001 | French et al. |
| 6,316,934 B1 | 11/2001 | Amorai-Moriya et al. |
| 6,416,327 B1 | 7/2002 | Wittenbecher |
| 6,428,449 B1 | 8/2002 | Apseloff |
| 6,516,222 B2 | 2/2003 | Fukuda |
| 6,663,491 B2 | 12/2003 | Watabe et al. |
| 6,743,167 B2 | 6/2004 | Balkin et al. |
| 6,746,371 B1 | 6/2004 | Brown et al. |
| 6,765,726 B2 | 7/2004 | French et al. |
| 6,788,200 B1 | 9/2004 | Jamel et al. |
| 6,817,979 B2 | 11/2004 | Nihtila |
| 6,820,025 B2 | 11/2004 | Bachmann et al. |
| 6,834,436 B2 | 12/2004 | Townsend et al. |
| 6,836,744 B1 | 12/2004 | Asphahani et al. |
| 6,856,852 B1 | 2/2005 | Bruinsma et al. |
| 6,876,496 B2 | 4/2005 | French et al. |
| 7,018,211 B1 | 3/2006 | Birkholzer et al. |
| 7,074,168 B1 | 7/2006 | Farnes et al. |
| 7,079,889 B2 | 7/2006 | Nakada |
| 7,089,216 B2 | 8/2006 | Van Overveld |
| 7,095,424 B2 | 8/2006 | Satoh et al. |
| 7,163,490 B2 | 1/2007 | Chen |
| 7,192,401 B2 | 3/2007 | Saalasti et al. |
| 7,254,516 B2 | 8/2007 | Case, Jr. et al. |
| 7,265,666 B2 | 9/2007 | Daniel |
| 7,315,249 B2 | 1/2008 | Littell |
| 7,359,121 B2 | 4/2008 | French et al. |
| 7,433,805 B2 | 10/2008 | Vock et al. |
| 7,442,131 B2 | 10/2008 | Milana |
| 7,493,232 B1 | 2/2009 | Surina |
| 7,497,807 B2 | 3/2009 | Neff et al. |
| 7,497,812 B2 | 3/2009 | Neff et al. |
| 7,556,590 B2 | 7/2009 | Watterson et al. |
| 7,602,301 B1 | 10/2009 | Stirling et al. |
| 7,628,730 B1 | 12/2009 | Watterson et al. |
| 7,676,332 B2 | 3/2010 | Damen |
| 7,717,858 B2 | 5/2010 | Massad |
| 7,736,272 B2 | 6/2010 | Martens |
| 7,771,293 B1 | 8/2010 | Vann |
| 7,771,320 B2 | 8/2010 | Riley et al. |
| 7,782,358 B2 | 8/2010 | Nieminen et al. |
| 7,783,347 B2 | 8/2010 | Abourizk et al. |
| 7,789,800 B1 | 9/2010 | Watterson et al. |
| 7,815,508 B2 | 10/2010 | Dohta |
| 7,821,407 B2 | 10/2010 | Shears et al. |
| 7,825,815 B2 | 11/2010 | Shears et al. |
| 7,846,067 B2 | 12/2010 | Hanoun |
| 7,846,069 B2 | 12/2010 | Martens |
| 7,857,708 B2 | 12/2010 | Ueda et al. |
| 7,894,849 B2 | 2/2011 | Kass et al. |
| 7,927,253 B2 | 4/2011 | Vincent et al. |
| 7,967,728 B2 * | 6/2011 | Zavadsky ............... A63F 9/24 482/5 |
| 7,978,081 B2 | 7/2011 | Shears et al. |
| 7,978,217 B2 | 7/2011 | Camhi |
| 7,985,164 B2 | 7/2011 | Ashby |
| 7,988,647 B2 | 8/2011 | Bunn et al. |
| 8,012,064 B2 | 9/2011 | Martens |
| 8,029,411 B2 | 10/2011 | Johnson |
| 8,038,549 B2 | 10/2011 | Vann |
| 8,038,578 B2 | 10/2011 | Olrik et al. |
| 3,083,643 A1 | 12/2011 | Ng et al. |
| 8,118,710 B2 | 2/2012 | Weinman et al. |
| 3,230,367 A1 | 7/2012 | Bell et al. |
| 8,235,870 B2 | 8/2012 | Hamilton |
| 8,269,826 B2 | 9/2012 | Nieminen et al. |
| 8,284,157 B2 | 10/2012 | Markovic et al. |
| 8,284,847 B2 | 10/2012 | Adermann |
| 8,409,057 B2 | 4/2013 | Martens |
| 3,435,177 A1 | 5/2013 | Lanfermann et al. |
| 8,460,199 B2 | 6/2013 | Rulkov et al. |
| 8,465,108 B2 | 6/2013 | Markovic et al. |
| 8,503,086 B2 | 8/2013 | French et al. |
| 8,523,667 B2 | 9/2013 | Clavin et al. |
| 8,568,277 B2 | 10/2013 | Johnson |
| 8,568,330 B2 | 10/2013 | Mollicone et al. |
| 8,589,114 B2 | 11/2013 | Papadourakis |
| 8,602,988 B2 | 12/2013 | Hunt et al. |
| 8,616,989 B2 | 12/2013 | Bentley |
| 8,676,541 B2 | 3/2014 | Schrock et al. |

(56) References Cited

U.S. PATENT DOCUMENTS

| | | | |
|---|---|---|---|
| 8,702,485 B2 | 4/2014 | Flury et al. | |
| 8,758,201 B2 | 6/2014 | Ashby et al. | |
| 8,784,270 B2 | 7/2014 | Ashby et al. | |
| 8,784,307 B1 | 7/2014 | Groteke et al. | |
| 8,812,428 B2 | 8/2014 | Mollicone et al. | |
| 8,854,304 B2 | 10/2014 | Nishimoto et al. | |
| 8,858,400 B2 | 10/2014 | Johnson | |
| 8,861,091 B2 | 10/2014 | French et al. | |
| 8,892,219 B2 | 11/2014 | Pryor | |
| 8,911,328 B2 * | 12/2014 | Alessandri | A63B 21/0628 482/8 |
| 8,928,484 B2 | 1/2015 | Chang et al. | |
| 9,008,973 B2 | 4/2015 | French | |
| 9,078,585 B2 | 7/2015 | Miyazaki et al. | |
| 9,141,759 B2 | 9/2015 | Burich et al. | |
| 9,149,222 B1 | 10/2015 | Zets et al. | |
| 9,154,739 B1 | 10/2015 | Nicolaou et al. | |
| 9,317,660 B2 | 4/2016 | Burich et al. | |
| 9,545,541 B2 | 1/2017 | Aragones et al. | |
| 9,630,059 B2 | 4/2017 | Burich et al. | |
| 2002/0019258 A1 | 2/2002 | Kim et al. | |
| 2002/0183961 A1 | 12/2002 | French et al. | |
| 2003/0040348 A1 | 2/2003 | Martens | |
| 2003/0054327 A1 | 3/2003 | Evensen | |
| 2003/0077556 A1 | 4/2003 | French et al. | |
| 2003/0214408 A1 | 11/2003 | Grajales et al. | |
| 2003/0228033 A1 | 12/2003 | Daniel et al. | |
| 2003/0228628 A1 | 12/2003 | Powell | |
| 2004/0087366 A1 | 5/2004 | Shum et al. | |
| 2004/0102931 A1 | 5/2004 | Ellis et al. | |
| 2004/0112151 A1 | 6/2004 | Maxwell et al. | |
| 2004/0162194 A1 | 8/2004 | Habing | |
| 2004/0219498 A1 | 11/2004 | Davidson | |
| 2004/0220856 A1 | 11/2004 | Moore | |
| 2004/0255490 A1 | 12/2004 | Wan et al. | |
| 2005/0001728 A1 | 1/2005 | Appelt et al. | |
| 2005/0079905 A1 | 4/2005 | Martens | |
| 2005/0085348 A1 | 4/2005 | Kiefer et al. | |
| 2005/0101887 A1 | 5/2005 | Stark et al. | |
| 2005/0107723 A1 | 5/2005 | Wehman et al. | |
| 2005/0113650 A1 | 5/2005 | Pacione et al. | |
| 2005/0113652 A1 | 5/2005 | Stark et al. | |
| 2005/0172311 A1 | 8/2005 | Hjelt et al. | |
| 2005/0182341 A1 | 8/2005 | Katayama et al. | |
| 2005/0196737 A1 | 9/2005 | Mann | |
| 2005/0209050 A1 | 9/2005 | Bartels | |
| 2005/0223799 A1 | 10/2005 | Murphy | |
| 2005/0239026 A1 | 10/2005 | Suzuki et al. | |
| 2005/0272517 A1 | 12/2005 | Funk et al. | |
| 2006/0025282 A1 | 2/2006 | Redmann | |
| 2006/0040793 A1 | 2/2006 | Martens | |
| 2006/0079800 A1 | 4/2006 | Martikka et al. | |
| 2006/0136173 A1 | 6/2006 | Case et al. | |
| 2006/0166737 A1 | 7/2006 | Bentley | |
| 2006/0173070 A1 | 8/2006 | Murase et al. | |
| 2006/0205569 A1 | 9/2006 | Watterson et al. | |
| 2006/0229170 A1 | 10/2006 | Ozawa et al. | |
| 2006/0241521 A1 | 10/2006 | Cohen | |
| 2006/0247070 A1 | 11/2006 | Funk et al. | |
| 2006/0262120 A1 | 11/2006 | Rosenberg | |
| 2006/0293617 A1 | 12/2006 | Einav et al. | |
| 2007/0050715 A1 | 3/2007 | Behar | |
| 2007/0118406 A1 | 5/2007 | Killin et al. | |
| 2007/0155588 A1 | 7/2007 | Stark et al. | |
| 2007/0177024 A1 | 8/2007 | Camhi | |
| 2007/0213178 A1 | 9/2007 | Lemmela | |
| 2007/0232453 A1 | 10/2007 | Hanoun | |
| 2007/0232455 A1 | 10/2007 | Hanoun | |
| 2007/0270214 A1 | 11/2007 | Bentley | |
| 2007/0271065 A1 | 11/2007 | Gupta et al. | |
| 2007/0272011 A1 | 11/2007 | Chapa et al. | |
| 2008/0033581 A1 | 2/2008 | Doshi et al. | |
| 2008/0096726 A1 | 4/2008 | Riley et al. | |
| 2008/0161733 A1 | 7/2008 | Einav et al. | |
| 2008/0189291 A1 | 8/2008 | Hsu | |
| 2008/0191864 A1 | 8/2008 | Wolfson | |
| 2008/0200312 A1 | 8/2008 | Tagliabue | |
| 2008/0212032 A1 | 9/2008 | Seiller et al. | |
| 2008/0221487 A1 | 9/2008 | Zohar et al. | |
| 2008/0246629 A1 | 10/2008 | Tsui et al. | |
| 2008/0254866 A1 | 10/2008 | Young et al. | |
| 2008/0267444 A1 | 10/2008 | Simons-Nikolova et al. | |
| 2008/0269016 A1 | 10/2008 | Ungari et al. | |
| 2008/0281550 A1 | 11/2008 | Hogle et al. | |
| 2009/0023555 A1 | 1/2009 | Raymond | |
| 2009/0042695 A1 | 2/2009 | Chien et al. | |
| 2009/0044429 A1 | 2/2009 | Cook | |
| 2009/0062092 A1 * | 3/2009 | Mortimer | A63B 26/003 482/142 |
| 2009/0069722 A1 | 3/2009 | Flaction et al. | |
| 2009/0098519 A1 | 4/2009 | Byerly | |
| 2009/0118100 A1 * | 5/2009 | Oliver | A63B 24/0062 482/8 |
| 2009/0149299 A1 | 6/2009 | Tchao et al. | |
| 2009/0171614 A1 | 7/2009 | Damen | |
| 2009/0209358 A1 | 8/2009 | Niegowski | |
| 2009/0227876 A1 | 9/2009 | Tran | |
| 2009/0233769 A1 * | 9/2009 | Pryor | B60R 11/0235 482/8 |
| 2009/0233770 A1 | 9/2009 | Vincent et al. | |
| 2009/0258710 A1 | 10/2009 | Quatrochi et al. | |
| 2009/0269728 A1 | 10/2009 | Verstegen et al. | |
| 2009/0298024 A1 | 12/2009 | Batzler et al. | |
| 2009/0298650 A1 | 12/2009 | Kutliroff | |
| 2009/0299232 A1 | 12/2009 | Lanfermann et al. | |
| 2010/0036288 A1 | 2/2010 | Lanfermann et al. | |
| 2010/0056340 A1 | 3/2010 | Ellis et al. | |
| 2010/0063778 A1 | 3/2010 | Schrock et al. | |
| 2010/0088023 A1 | 4/2010 | Werner | |
| 2010/0094174 A1 | 4/2010 | Choi et al. | |
| 2010/0125026 A1 | 5/2010 | Zavadsky et al. | |
| 2010/0125028 A1 | 5/2010 | Heppert | |
| 2010/0137748 A1 | 6/2010 | Sone et al. | |
| 2010/0144414 A1 | 6/2010 | Edis et al. | |
| 2010/0197462 A1 | 8/2010 | Piane, Jr. | |
| 2010/0204616 A1 | 8/2010 | Shears et al. | |
| 2010/0205542 A1 | 8/2010 | Walman | |
| 2010/0210359 A1 | 8/2010 | Krzeslo et al. | |
| 2010/0210975 A1 | 8/2010 | Anthony, III et al. | |
| 2010/0217738 A1 | 8/2010 | Sarel | |
| 2010/0227302 A1 | 9/2010 | McGilvery et al. | |
| 2010/0234184 A1 | 9/2010 | Le Page et al. | |
| 2010/0248901 A1 | 9/2010 | Martens | |
| 2010/0302142 A1 | 12/2010 | French et al. | |
| 2010/0306712 A1 * | 12/2010 | Snook | G06K 9/00342 715/863 |
| 2010/0316983 A1 | 12/2010 | Johns, Jr. | |
| 2010/0332243 A1 | 12/2010 | Weigman et al. | |
| 2011/0027135 A1 | 2/2011 | Michiaki et al. | |
| 2011/0072457 A1 | 3/2011 | Lanfermann et al. | |
| 2011/0077129 A1 | 3/2011 | Martens | |
| 2011/0111922 A1 | 5/2011 | Weinman et al. | |
| 2011/0111924 A1 | 5/2011 | Jones et al. | |
| 2011/0112771 A1 | 5/2011 | French | |
| 2011/0131005 A1 | 6/2011 | Ueshima et al. | |
| 2011/0136627 A1 | 6/2011 | Williams | |
| 2011/0158912 A1 | 6/2011 | Wright et al. | |
| 2011/0212791 A1 | 9/2011 | Ueda et al. | |
| 2011/0224557 A1 | 9/2011 | Banet et al. | |
| 2011/0229864 A1 | 9/2011 | Short et al. | |
| 2011/0251021 A1 | 10/2011 | Zavadsky et al. | |
| 2011/0251495 A1 | 10/2011 | Province et al. | |
| 2011/0270135 A1 | 11/2011 | Dooley et al. | |
| 2011/0275907 A1 | 11/2011 | Inciardi et al. | |
| 2011/0304497 A1 | 12/2011 | Molyneux et al. | |
| 2011/0306491 A1 | 12/2011 | Belisle | |
| 2011/0307821 A1 | 12/2011 | Martens | |
| 2012/0034971 A1 | 2/2012 | Harp et al. | |
| 2012/0038627 A1 | 2/2012 | Sung et al. | |
| 2012/0052972 A1 | 3/2012 | Bentley | |
| 2012/0130515 A1 * | 5/2012 | Homsi | G09B 19/0038 700/91 |
| 2012/0130886 A1 | 5/2012 | Shergill et al. | |
| 2012/0143064 A1 | 6/2012 | Cyphery et al. | |

(56) References Cited

U.S. PATENT DOCUMENTS

| | | | |
|---|---|---|---|
| 2012/0143358 A1 | 6/2012 | Adams et al. |
| 2012/0150074 A1 | 6/2012 | Yanev et al. |
| 2012/0165703 A1 | 6/2012 | Bottum et al. |
| 2012/0183939 A1 | 7/2012 | Aragones et al. |
| 2012/0183940 A1 | 7/2012 | Aragones et al. |
| 2012/0190505 A1 | 7/2012 | Shavit et al. |
| 2012/0234111 A1 | 9/2012 | Molyneux et al. |
| 2012/0253484 A1 | 10/2012 | Burich et al. |
| 2012/0254934 A1 | 10/2012 | McBrearty et al. |
| 2012/0268592 A1 | 10/2012 | Aragones et al. |
| 2012/0271143 A1 | 10/2012 | Aragones et al. |
| 2012/0277891 A1 | 11/2012 | Aragones et al. |
| 2012/0315986 A1 | 12/2012 | Walling |
| 2012/0315987 A1 | 12/2012 | Walling |
| 2013/0019694 A1 | 1/2013 | Molyneux et al. |
| 2013/0022947 A1 | 1/2013 | Simas et al. |
| 2013/0022950 A1 | 1/2013 | Muniz Simas et al. |
| 2013/0108993 A1 | 5/2013 | Katz |
| 2013/0171596 A1 | 7/2013 | French |
| 2013/0268205 A1 | 10/2013 | Aragones et al. |
| 2013/0281796 A1 | 10/2013 | Pan |
| 2013/0295539 A1 | 11/2013 | Wilson et al. |
| 2013/0324368 A1 | 12/2013 | Aragones et al. |
| 2013/0338802 A1 | 12/2013 | Winsper et al. |
| 2014/0073486 A1 | 3/2014 | Ahmed et al. |
| 2014/0278218 A1 | 9/2014 | Chang |
| 2015/0105881 A1 | 4/2015 | Guerrero et al. |

FOREIGN PATENT DOCUMENTS

| | | | |
|---|---|---|---|
| CN | 1933880 A | 3/2007 |
| CN | 101668482 A | 3/2010 |
| CN | 201643611 U | 11/2010 |
| CN | 101964047 A | 2/2011 |
| CN | 103154954 A | 6/2013 |
| CN | 103493056 A | 1/2014 |
| DE | 29720110 U1 | 1/1998 |
| GB | 2415788 A | 1/2006 |
| JP | H8-57093 A | 3/1996 |
| JP | 857093 | 5/1996 |
| JP | 2000033184 A | 2/2000 |
| JP | 2000070242 A | 3/2000 |
| JP | 2000504854 A | 4/2000 |
| JP | 2001224853 A | 8/2001 |
| JP | 2001231904 A | 8/2001 |
| JP | 2001299975 A | 10/2001 |
| JP | 2002112984 A | 4/2002 |
| JP | 2002516121 A | 6/2002 |
| JP | 2002253718 A | 9/2002 |
| JP | 2002291952 A | 10/2002 |
| JP | 2003085288 A | 3/2003 |
| JP | 2003290406 A | 10/2003 |
| JP | 2004089727 A | 3/2004 |
| JP | 2004097649 A | 4/2004 |
| JP | 2004208995 A | 7/2004 |
| JP | 2005034195 A | 2/2005 |
| JP | 3656853 B2 | 6/2005 |
| JP | 2005198818 A | 7/2005 |
| JP | 2006130127 A | 5/2006 |
| JP | 2006167313 A | 6/2006 |
| JP | 2006263002 A | 10/2006 |
| JP | 2006320424 A | 11/2006 |
| JP | 2007143748 A | 6/2007 |
| JP | 2007144107 A | 6/2007 |
| JP | 2007260307 A | 10/2007 |
| JP | 2008104758 A | 5/2008 |
| JP | 2008295746 A | 12/2008 |
| JP | 2009048757 A | 3/2009 |
| JP | 2009050699 A | 3/2009 |
| JP | 2009078134 A | 4/2009 |
| JP | 2009172315 A | 8/2009 |
| JP | 2009201672 A | 9/2009 |
| JP | 2009213656 A | 9/2009 |
| JP | 2009213782 A | 9/2009 |
| JP | 2009219828 A | 10/2009 |
| JP | 2009247836 A | 10/2009 |
| JP | 2009279041 A | 12/2009 |
| JP | 2010502368 A | 1/2010 |
| JP | 2010075715 A | 4/2010 |
| JP | 2010086358 A | 4/2010 |
| JP | 2010188159 A | 9/2010 |
| JP | 2010246636 A | 11/2010 |
| KR | 20030041034 A | 5/2003 |
| KR | 20090084035 A | 8/2009 |
| KR | 20100086052 A | 7/2010 |
| WO | 9729814 A1 | 8/1997 |
| WO | 2004073494 A2 | 9/2004 |
| WO | 2006098282 A1 | 9/2006 |
| WO | 2009043024 A1 | 4/2009 |
| WO | 2009073607 A2 | 6/2009 |
| WO | 2010121166 A1 | 10/2010 |
| WO | 2012021633 A2 | 2/2012 |
| WO | 2012039467 A1 | 3/2012 |
| WO | 2012061438 A2 | 5/2012 |
| WO | 2012061804 A1 | 5/2012 |
| WO | 2012071548 A1 | 5/2012 |
| WO | 2012071551 A1 | 5/2012 |

OTHER PUBLICATIONS

May 31, 2013 (WO)—International Search Report and Written Opinion—App. No. PCT/US2012/066070.

May 29, 2013 (WO)—International Search Report and Written Opinion—App. No. PCT/US2012/066065.

Jun. 6, 2013 (WO)—International Preliminary Report on Patentability—App. No. PCT/US20111062117.

May 16, 2013 (WO)—International Preliminary Report on Patentability—App. No. PCT/US20111059559.

Apr. 3, 2012—(WO) ISR &WO—App. No. PCT/US11/1064711.

Feb. 23, 2012—(WO) ISR & WO—App. No. PCT/US2011/062117.

Feb. 20, 2014 (WO)—International Search Report and Written Opinion—App. No. PCT/US2013/067512.

Sep. 12, 2013—(WO) ISR & WO—App. No. PCT/US2013/044109.

Zhao, et al., Design and Practice for Individual Specialized PC Expert System for College Student, Journal of Xi An Institute of Physical Education, vol. 22, No. 2 (Mar. 2005) pp. 118-121.

Plagge et al: "Design and Evaluation of the T-Team of the University of Tuebingen for RoboCup '98" in "Network and Parallel Computing", Jan. 1, 1999 (Jan. 1, 1999), Springer Inernational Publishing, Cham 032548, XP055334016, ISSN: 0302-9743, ISBN: 978-3-642-23677-8, vol. 1604, pp. 464-472, DOI: 40.1007/3-540-48422-1_47.

Translation of JP2009201672A, Published Sep. 10, 2009 [Retrieved Oct. 11, 2017] Retrieved from Google Patents <URL:https://patents.google.com/patent/JP2009201672A/en>.

Autotranslation of JP2009-201672, published Sep. 10, 2009 [Retrieved Oct. 13, 2017] Retrieved from JPO using AIPN system.

* cited by examiner

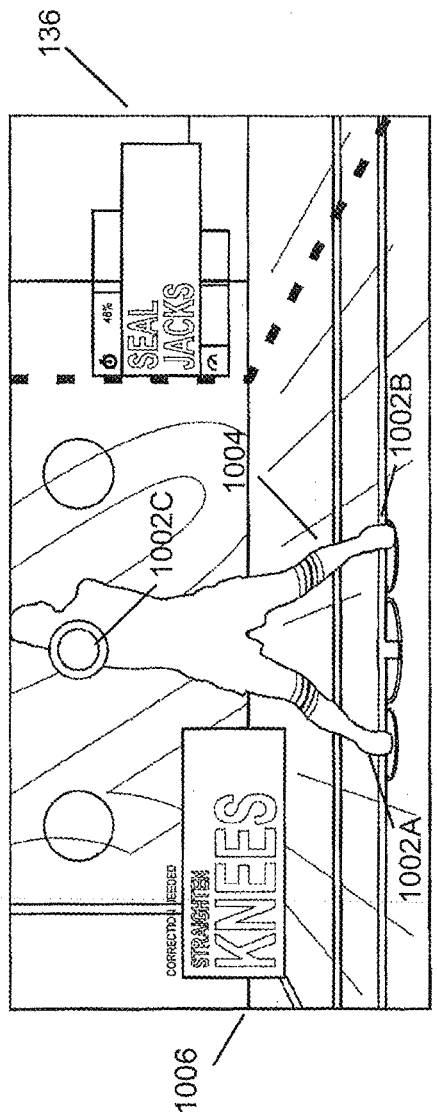
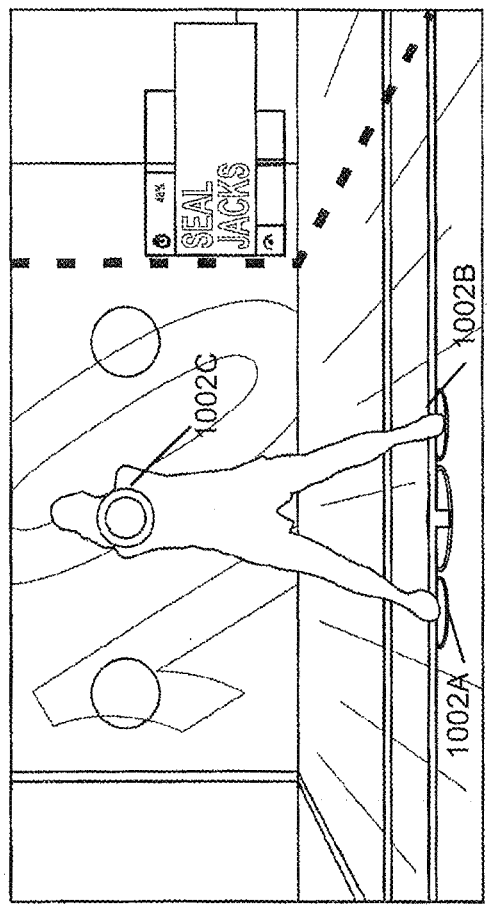
FIG. 10A
FIG. 10B

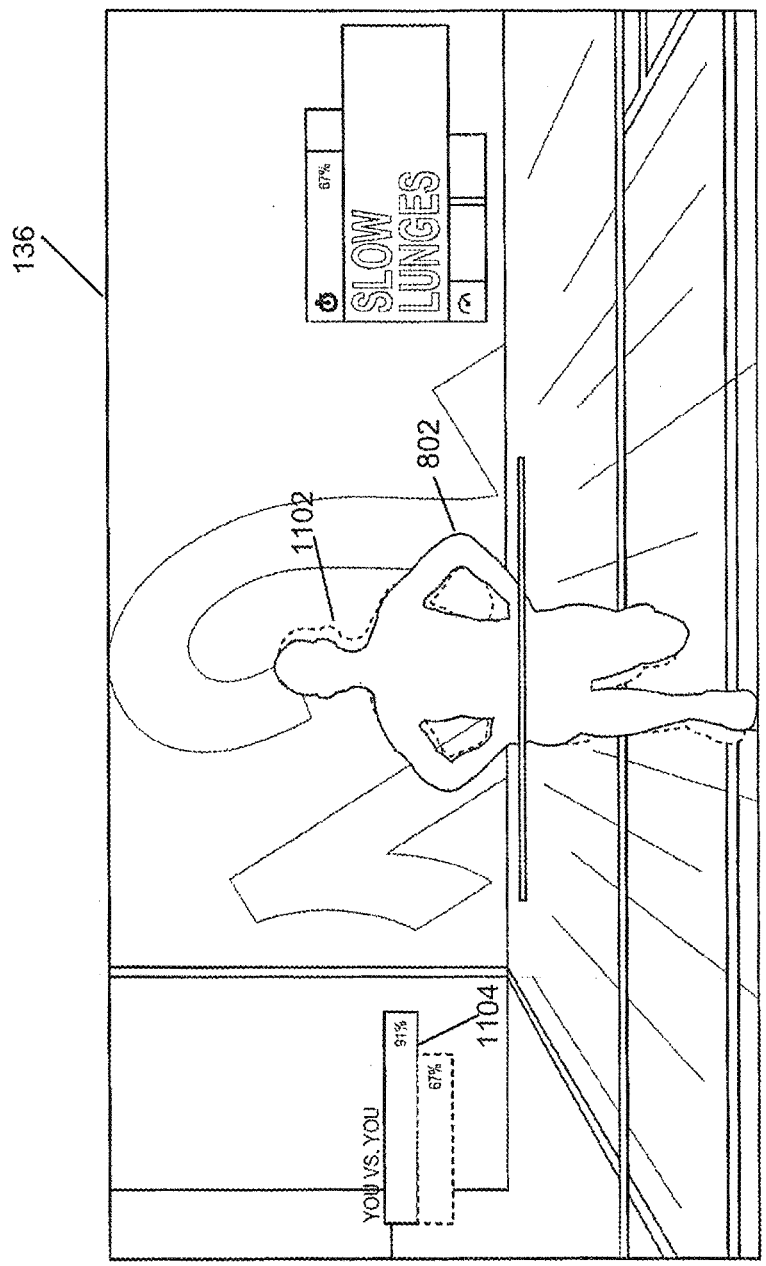

Prompt a first user to perform at least one exercise during a workout session
1802

Monitor the first user performing the at least one exercise
1804

Generate a first virtual avatar of the first user based on user data captured by the monitoring device
1806

Generate a first virtual shadow for the first virtual avatar that is based on attributes relating to the first user
1808

Receive second user data corresponding to a second user for generating a second virtual avatar and a second virtual shadow
1810

Display simultaneously on a display device the first and second virtual avatars and the first and second virtual shadows
1812

FIG. 18

METHOD AND SYSTEM FOR AUTOMATED PERSONAL TRAINING

CROSS REFERENCE TO RELATED APPLICATIONS

This application is a continuation of U.S. patent application Ser. No. 15/174,665, filed Jun. 6, 2016, which is a continuation of U.S. patent application Ser. No. 13/290,478, filed Nov. 7, 2011, now U.S. Pat. No. 9,358,426 on Jun. 7, 2016, and which claims the benefit of and priority to U.S. Provisional Patent Application Nos. 61/410,777 filed Nov. 5, 2010, 61/417,102 filed Nov. 24, 2010, 61/422,511 filed Dec. 13, 2010, 61/432,472 filed Jan. 13, 2011, and 61/433,792 filed Jan. 18, 2011, each of which is entitled "Method and System for Automated Personal Training." The content of each of the applications is expressly incorporated herein by reference in its entirety for any and all non-limiting purposes.

BACKGROUND

While most people appreciate the importance of physical fitness, many have difficulty finding the motivation required to maintain a regular exercise program. Some people find it particularly difficult to maintain an exercise regimen that involves continuously repetitive motions, such as running, walking and bicycling.

Additionally, individuals may view exercise as work or a chore and thus, separate it from enjoyable aspects of their daily lives. Often, this separation between athletic activity and other activities reduces the amount of motivation that an individual might have toward exercising. Further, athletic activity services and systems directed toward encouraging individuals to engage in athletic activities might also be too focused on one or more particular activities while an individual's interests are ignored. This may further decrease a user's interest in participating in athletic activities or using the athletic activity services and systems.

Therefore, improved systems and methods to address these and other shortcomings in the art are desired.

BRIEF SUMMARY

The following presents a simplified summary in order to provide a basic understanding of some aspects of the disclosure. The summary is not an extensive overview of the disclosure. It is neither intended to identify key or critical elements of the disclosure nor to delineate the scope of the disclosure. The following summary merely presents some concepts of the disclosure in a simplified form as a prelude to the description below.

Aspects of this disclosure relate to motivating individuals to obtain or maintain a threshold level of physical activity. Certain implementations may motivate individuals to participate in a regular exercise program. In one embodiment, feedback may facilitate individuals observing one or more benefits associated with physical activity. By realizing benefits associated with their activities, users may be encouraged to continue exercising, such as through participation in one or more regular activities.

Example embodiments may relate to a system, method, apparatus, and computer readable media configured for monitoring a user performing an exercise and generating a representation of a user and a virtual shadow. According to one implementation, the virtual shadow may illustrate a proper form (or any specific form) of the exercise. The example embodiments may further be configured for determining an amount of overlap between the user representation and the virtual shadow, and generating a feedback score based on the amount of overlap.

These and other aspects of the embodiments are discussed in greater detail throughout this disclosure, including the accompanying drawings.

BRIEF DESCRIPTION OF THE DRAWINGS

The present disclosure is illustrated by way of example and not limited in the accompanying figures in which like reference numerals indicate similar elements and in which:

FIGS. 1A-B illustrate an example of a system for providing personal training in accordance with example embodiments, wherein FIG. 1A illustrates an example network configured to monitor athletic activity, and FIG. 1B illustrates an example computing device in accordance with example embodiments.

FIGS. 8, 9, and 10A-10B illustrate example displays of a user avatar performing an exercise in accordance with example embodiments.

FIGS. 11-12 illustrate example displays each including a virtual shadow for a user avatar in accordance with example embodiments.

FIG. 18 illustrates an example flow diagram of a method for providing virtual competition in a virtual environment between multiple virtual avatars, in accordance with one or more example embodiments.

DETAILED DESCRIPTION

In the following description of the various embodiments, reference is made to the accompanying drawings, which form a part hereof, and in which is shown by way of illustration various embodiments in which the disclosure may be practiced. It is to be understood that other embodiments may be utilized and structural and functional modifications may be made without departing from the scope and spirit of the present disclosure. Further, headings within this disclosure should not be considered as limiting aspects of the disclosure. Those skilled in the art with the benefit of this disclosure will appreciate that the example embodiments are not limited to the example headings.

I. Example Personal Training System

A. Illustrative Computing Devices

Figure 1A:
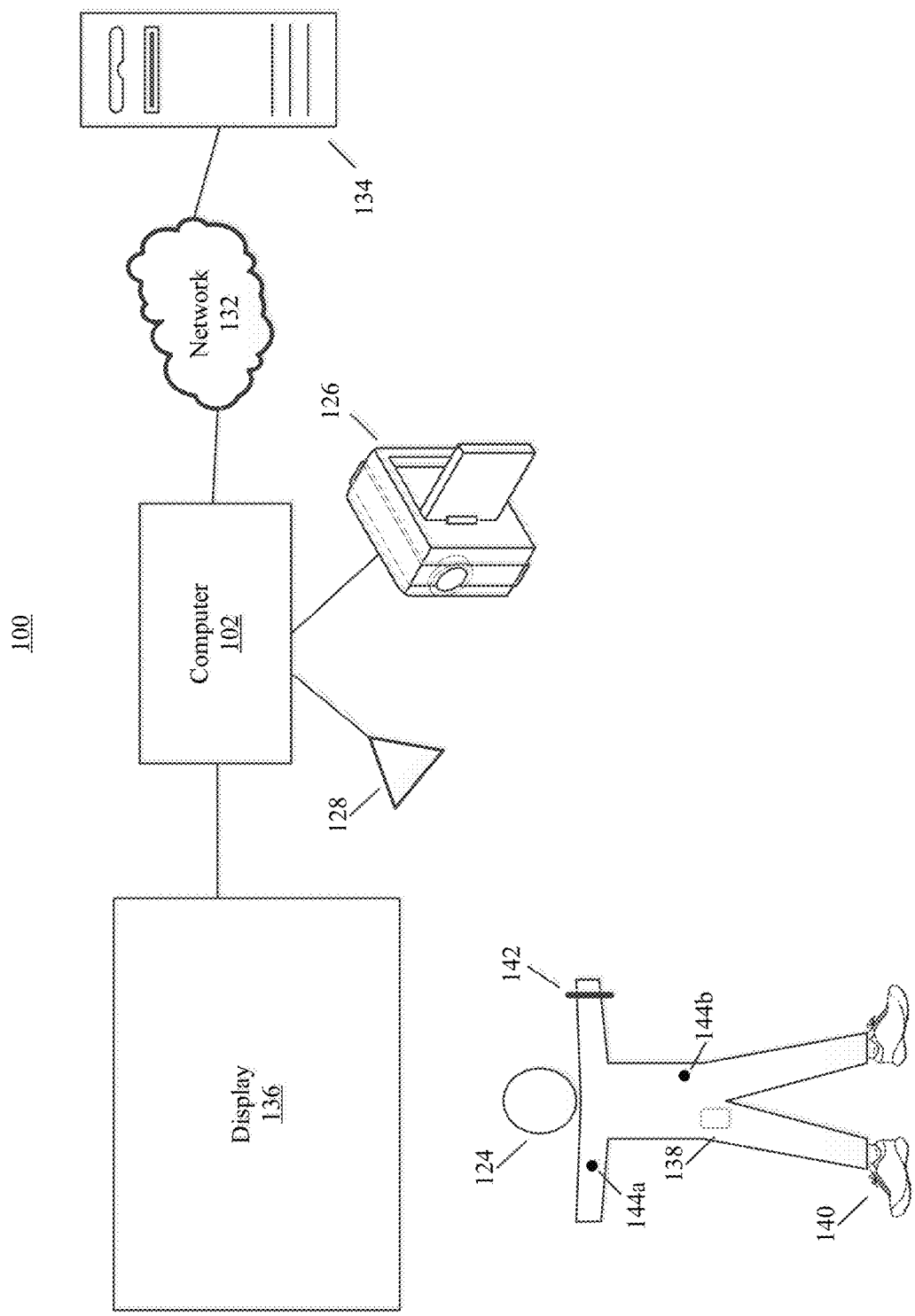

FIG. 1A illustrates an example of a personal training system 100 in accordance with example embodiments. Example system 100 may include one or more electronic devices, such as computer 102. Computer 102 may comprise a mobile terminal, such as a telephone, music player, tablet, netbook or any portable device. In other embodiments, computer 102 may comprise a set-top box (STB), desktop computer, digital video recorder(s) (DVR), computer server(s), and/or any other desired computing device. In certain configurations, computer 102 may comprise a gaming console, such as for example, a Microsoft® XBOX, Sony® Playstation, and/or a Nintendo® Wii gaming consoles. Those skilled in the art will appreciate that these are merely example consoles for descriptive purposes and this disclosure is not limited to any console or device.

Figure 1B:
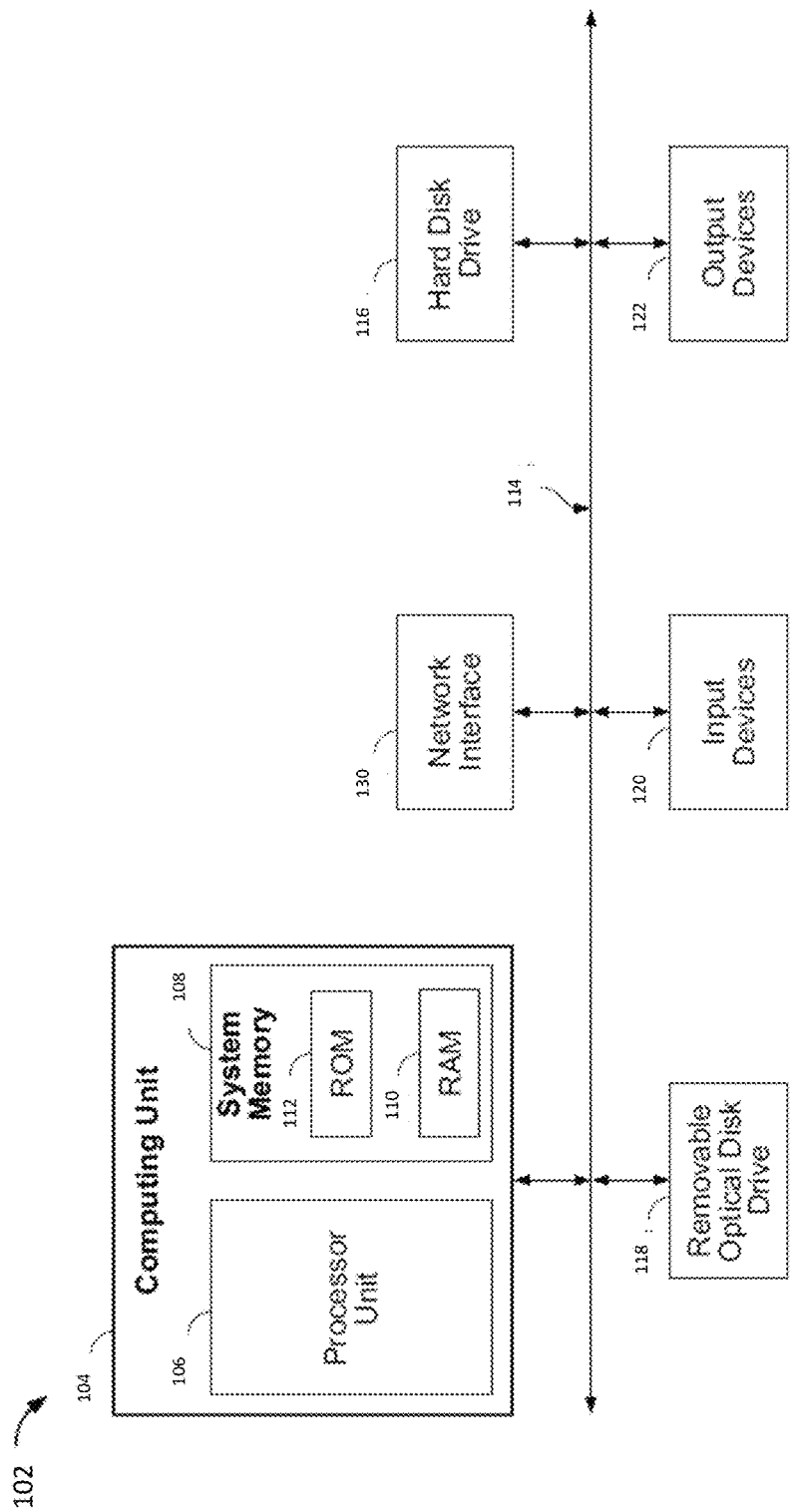

Turning briefly to FIG. 1B, computer 102 may include computing unit 104, which may comprise at least one processing unit 106. Processing unit 106 may be any type of processing device for executing software instructions, such as for example, a microprocessor device. Computer 102 may include a variety of non-transitory computer readable media, such as memory 108. Memory 108 may include, but is not limited to, random access memory (RAM) such as RAM 110, and/or read only memory (ROM), such as ROM 112. Memory 108 may include any of: electronically erasable programmable read only memory (EEPROM), flash memory or other memory technology, CD-ROM, digital versatile disks (DVD) or other optical disk storage, magnetic storage devices, or any other medium that can be used to store the desired information and that can be accessed by computer 102.

The processing unit 106 and the system memory 108 may be connected, either directly or indirectly, through a bus 114 or alternate communication structure to one or more peripheral devices. For example, the processing unit 106 or the system memory 108 may be directly or indirectly connected to additional memory storage, such as a hard disk drive 116, a removable magnetic disk drive, an optical disk drive 118, and a flash memory card, as well as to input devices 120, and output devices 122. The processing unit 106 and the system memory 108 also may be directly or indirectly connected to one or more input devices 120 and one or more output devices 122. The output devices 122 may include, for example, a monitor display, television, printer, stereo, or speakers. The input devices 120 may include, for example, a keyboard, touch screen, a remote control pad, a pointing device (such as a mouse, touchpad, stylus, trackball, or joystick), a scanner, a camera or a microphone. In this regard, input devices 120 may comprise one or more sensors configured to sense, detect, and/or measure athletic movement from a user, such as user 124, shown in FIG. 1A.

Looking again to FIG. 1A, image-capturing device 126 and/or sensor 128 may be utilized in detecting and/or measuring athletic movements of user 124. In one embodiment, data obtained image-capturing device 126 or sensor 128 may directly detect athletic movements, such that the data obtained from image-capturing device 126 or sensor 128 is directly correlated to a motion parameter. For example, and with reference to FIG. 4, image data from image-capturing device 126 may detect that the distance between sensor locations 402g and 402i has decreased and therefore, image-capturing device 126 alone may be configured to detect that user's 124 right arm has moved. Yet, in other embodiments, data from image-capturing device 126 and/or sensor 128 may be utilized in combination, either with each other or with other sensors to detect and/or measure movements. Thus, certain measurements may be determined from combining data obtained from two or more devices. Image-capturing device 126 and/or sensor 128 may include or be operatively connected to one or more sensors, including but not limited to: an accelerometer, a gyroscope, a location-determining device (e.g., GPS), light sensor, temperature sensor (including ambient temperature and/or body temperature), heart rate monitor, image-capturing sensor, moisture sensor and/or combinations thereof. Example uses of illustrative sensors 126, 128 are provided below in Section I.C, entitled "Illustrative Sensors." Computer 102 may also use touch screens or image capturing device to determine where a user is pointing to make selections from a graphical user interface. One or more embodiments may utilize one or more wired and/or wireless technologies, alone or in combination, wherein examples of wireless technologies include Bluetooth® technologies, Bluetooth® low energy technologies, and/or ANT technologies.

B. Illustrative Network

Still further, computer 102, computing unit 104, and/or any other electronic devices may be directly or indirectly connected to one or more network interfaces, such as example interface 130 (shown in FIG. 1B) for communicating with a network, such as network 132. In the example of FIG. 1B, network interface 130, may comprise a network adapter or network interface card (NIC) configured to translate data and control signals from the computing unit 104 into network messages according to one or more communication protocols, such as the Transmission Control Protocol (TCP), the Internet Protocol (IP), and the User Datagram Protocol (UDP). These protocols are well known in the art, and thus will not be discussed here in more detail. An interface 130 may employ any suitable connection agent for connecting to a network, including, for example, a wireless transceiver, a power line adapter, a modem, or an Ethernet connection. Network 132, however, may be any one or more information distribution network(s), of any type(s) or topography(s), alone or in combination(s), such as internet(s), intranet(s), cloud(s), LAN(s). Network 132 may be any one or more of cable, fiber, satellite, telephone, cellular, wireless, etc. Networks are well known in the art, and thus will not be discussed here in more detail. Network 132 may be variously configured such as having one or more wired or wireless communication channels to connect one or more locations (e.g., schools, businesses, homes, consumer dwellings, network resources, etc.), to one or more remote servers 134, or to other computers, such as similar or identical to computer 102. Indeed, system 100 may include more than one instance of each component (e.g., more than one computer 102, more than one display 136, etc.).

Regardless of whether computer 102 or other electronic device within network 132 is portable or at a fixed location, it should be appreciated that, in addition to the input, output and storage peripheral devices specifically listed above, the computing device may be connected, such as either directly, or through network 132 to a variety of other peripheral devices, including some that may perform input, output and storage functions, or some combination thereof. In certain embodiments, a single device may integrate one or more components shown in FIG. 1A. For example, a single device may include computer 102, image-capturing device 126, sensor 128, display 136 and/or additional components. In one embodiment, sensor device 138 may comprise a mobile terminal having a display 136, image-capturing device 126, and one or more sensors 128. Yet, in another embodiment, image-capturing device 126, and/or sensor 128 may be peripherals configured to be operatively connected to a media device, including for example, a gaming or media system. Thus, it goes from the foregoing that this disclosure is not limited to stationary systems and methods. Rather, certain embodiments may be carried out by a user 124 in almost any location.

C. Illustrative Sensors

Computer 102 and/or other devices may comprise one or more sensors 126, 128 configured to detect and/or monitor at least one fitness parameter of a user 124. Sensors 126 and/or 128, may include but not limited to: an accelerometer, a gyroscope, a location-determining device (e.g., GPS), light sensor, temperature sensor (including ambient temperature and/or body temperature), heart rate monitor, image-capturing sensor, moisture sensor and/or combinations thereof. Network 132 and/or computer 102 may be in communication with one or more electronic devices of system 100, including for example, display 136, an image capturing device 126 (e.g., one or more video cameras), and sensor 128, which may be an infrared (IR) device. In one embodiment sensor 128 may comprise an IR transceiver. For example, sensors 126, and/or 128 may transmit waveforms into the environment, including towards the direction of user 124 and receive a "reflection" or otherwise detect alterations of those released waveforms. In yet another embodiment, image-capturing device 126 and/or sensor 128 may be configured to transmit and/or receive other wireless signals, such as radar, sonar, and/or audible information. Those skilled in the art will readily appreciate that signals corresponding to a multitude of different data spectrums may be utilized in accordance with various embodiments. In this regard, sensors 126 and/or 128 may detect waveforms emitted from external sources (e.g., not system 100). For example, sensors 126 and/or 128 may detect heat being emitted from user 124 and/or the surrounding environment. Thus, image-capturing device 126 and/or sensor 128 may comprise one or more thermal imaging devices. In one embodiment, image-capturing device 126 and/or sensor 128 may comprise an IR device configured to perform range phenomenology. As a non-limited example, image-capturing devices configured to perform range phenomenology are commercially available from Flir Systems, Inc. of Portland, Oreg. Although image capturing device 126 and sensor 128 and display 136 are shown in direct (wirelessly or wired) communication with computer 102, those skilled in the art will appreciate that any may directly communicate (wirelessly or wired) with network 132.

1. Multi-Purpose Electronic Devices

User 124 may possess, carry, and/or wear any number of electronic devices, including sensory devices 138, 140, 142, and/or 144. In certain embodiments, one or more devices 138, 140, 142, 144 may not be specially manufactured for fitness or athletic purposes. Indeed, aspects of this disclosure relate to utilizing data from a plurality of devices, some of which are not fitness devices, to collect, detect, and/or measure athletic data. In one embodiment, device 138 may comprise a portable electronic device, such as a telephone or digital music player, including an IPOD®, IPAD®, or iPhone®, brand devices available from Apple, Inc. of Cupertino, Calif. or Zune® or Microsoft® Windows devices available from Microsoft of Redmond, Wash. As known in the art, digital media players can serve as both an output device for a computer (e.g., outputting music from a sound file or pictures from an image file) and a storage device. In one embodiment, device 138 may be computer 102, yet in other embodiments, computer 102 may be entirely distinct from device 138. Regardless of whether device 138 is configured to provide certain output, it may serve as an input device for receiving sensory information. Devices 138, 140, 142, and/or 144 may include one or more sensors, including but not limited to: an accelerometer, a gyroscope, a location-determining device (e.g., GPS), light sensor, temperature sensor (including ambient temperature and/or body temperature), heart rate monitor, image-capturing sensor, moisture sensor and/or combinations thereof. In certain embodiments, sensors may be passive, such as reflective materials that may be detected by image-capturing device 126 and/or sensor 128 (among others). In certain embodiments, sensors 144 may be integrated into apparel, such as athletic clothing. For instance, the user 124 may wear one or more on-body sensors 144a-b. Sensors 144 may be incorporated into the clothing of user 124 and/or placed at any desired location of the body of user 124. Sensors 144 may communicate (e.g., wirelessly) with computer 102, sensors 128, 138, 140, and 142, and/or camera 126. Examples of interactive gaming apparel are described in U.S. patent application Ser. No. 10/286,396, filed Oct. 30, 2002, and published as U.S. Pat. Pub, No. 2004/0087366, the contents of which are incorporated herein by reference in its entirety for any and all non-limiting purposes. In certain embodiments, passive sensing surfaces may reflect waveforms, such as infrared light, emitted by image-capturing device 126 and/or sensor 128. In one embodiment, passive sensors located on user's 124 apparel may comprise generally spherical structures made of glass or other transparent or translucent surfaces which may reflect waveforms. Different classes of apparel may be utilized in which a given class of apparel has specific sensors configured to be located proximate to a specific portion of the user's 124 body when properly worn. For example, golf apparel may include one or more sensors positioned on the apparel in a first configuration and yet soccer apparel may include one or more sensors positioned on apparel in a second configuration. For example, looking briefly to FIG. 14, golf apparel may have more sensors positioned about regions 1402A and 1402D than apparel for soccer, which may have more sensors (and/or different types of sensors) positioned about regions 1402C and 1402F). Devices 138-144 may communicate with each other, either directly or through a network, such as network 132. Communication between one or more of devices 138-144 may communicate through computer 102. For example, two or more of devices 138-144 may be peripherals operatively connected to bus 114 of computer 102. In yet another embodiment, a first device, such as device 138 may communicate with a first computer, such as computer 102 as well as another device, such as device 142, however, device 142 may not be configured to connect to computer 102 but may communicate with device 138. Those skilled in the art will appreciate that other configurations are possible.

Some implementations of the example embodiments may alternately or additionally employ computing devices that are intended to be capable of a wide variety of functions, such as a desktop or laptop personal computer. These computing devices may have any combination of peripheral devices or additional components as desired. Also, the components shown in FIG. 1B may be included in the server 134, other computers, apparatuses, etc.

2. Illustrative Apparel/Accessory Sensors

In certain embodiments, sensory devices 138, 140, 142 and/or 144 may be formed within or otherwise associated with user's 124 clothing or accessories, including a watch, armband, wristband, necklace, shirt, shoe, or the like. Examples of shoe-mounted and wrist-worn devices (devices 140 and 142, respectively) are described immediately below, however, these are merely example embodiments and this disclosure should not be limited to such.

i. Shoe-mounted Device

In certain embodiments, sensory device 140 may comprise footwear which may include one or more sensors, including but not limited to: an accelerometer, location-sensing components, such as GPS, and/or a force sensor system. FIG. 2A illustrates one exemplary embodiment of an example sensor system 202. In certain embodiments, system 202 may include a sensor assembly 204. Assembly 204 may comprise one or more sensors, such as for example, an accelerometer, location-determining components, and/or force sensors. In the illustrated embodiment, assembly 204 incorporates a plurality of sensors, which may include force-sensitive resistor (FSR) sensors 206. In yet other embodiments, other sensor(s) may be utilized. Port 208 may be positioned within a sole structure 209 of a shoe. Port 208 may optionally be provided to be in communication with an electronic module 210 (which may be in a housing 211) and a plurality of leads 212 connecting the FSR sensors 206 to the port 208. Module 210 may be contained within a well or cavity in a sole structure of a shoe. The port 208 and the module 210 include complementary interfaces 214, 216 for connection and communication.

In certain embodiments, at least one force-sensitive resistor 206 shown in FIG. 2A may contain first and second electrodes or electrical contacts 218, 220 and a force-sensitive resistive material 222 and/or 224 disposed between the electrodes 218, 220 to electrically connect the electrodes 218, 220 together. When pressure is applied to the force-sensitive material 222/224, the resistivity and/or conductivity of the force-sensitive material 222/224 changes, which changes the electrical potential between the electrodes 218, 220. The change in resistance can be detected by the sensor system 202 to detect the force applied on the sensor 216. The force-sensitive resistive material 222/224 may change its resistance under pressure in a variety of ways. For example, the force-sensitive material 222/224 may have an internal resistance that decreases when the material is compressed, similar to the quantum tunneling composites described in greater detail below. Further compression of this material may further decrease the resistance, allowing quantitative measurements, as well as binary (on/off) measurements. In some circumstances, this type of force-sensitive resistive behavior may be described as "volume-based resistance," and materials exhibiting this behavior may be referred to as "smart materials." As another example, the material 222/224 may change the resistance by changing the degree of surface-to-surface contact. This can be achieved in several ways, such as by using microprojections on the surface that raise the surface resistance in an uncompressed condition, where the surface resistance decreases when the microprojections are compressed, or by using a flexible electrode that can be deformed to create increased surface-to-surface contact with another electrode. This surface resistance may be the resistance between the material 222 and the electrode 218, 220 and/or the surface resistance between a conducting layer (e.g. carbon/graphite) and a force-sensitive layer (e.g. a semiconductor) of a multi-layer material 222/224. The greater the compression, the greater the surface-to-surface contact, resulting in lower resistance and enabling quantitative measurement. In some circumstances, this type of force-sensitive resistive behavior may be described as "contact-based resistance." It is understood that the force-sensitive resistive material 222/224, as defined herein, may be or include a doped or non-doped semiconducting material.

The electrodes 218, 220 of the FSR sensor 206 can be formed of any conductive material, including metals, carbon/graphite fibers or composites, other conductive composites, conductive polymers or polymers containing a conductive material, conductive ceramics, doped semiconductors, or any other conductive material. The leads 212 can be connected to the electrodes 218, 220 by any suitable method, including welding, soldering, brazing, adhesively joining, fasteners, or any other integral or non-integral joining method. Alternately, the electrode 218, 220 and associated lead(s) 212 may be formed of a single piece of the same material 222/224. In further embodiments, material 222 is configured to have at least one electric property (e.g., conductivity, resistance, etc.) than material 224. Examples of exemplary sensors are disclosed in U.S. patent application Ser. No. 12/483,824, filed on Jun. 12, 2009, the contents of which are incorporated herein in their entirety for any and all non-limiting purposes.

ii. Wrist-Worn Device

Figure 2B:
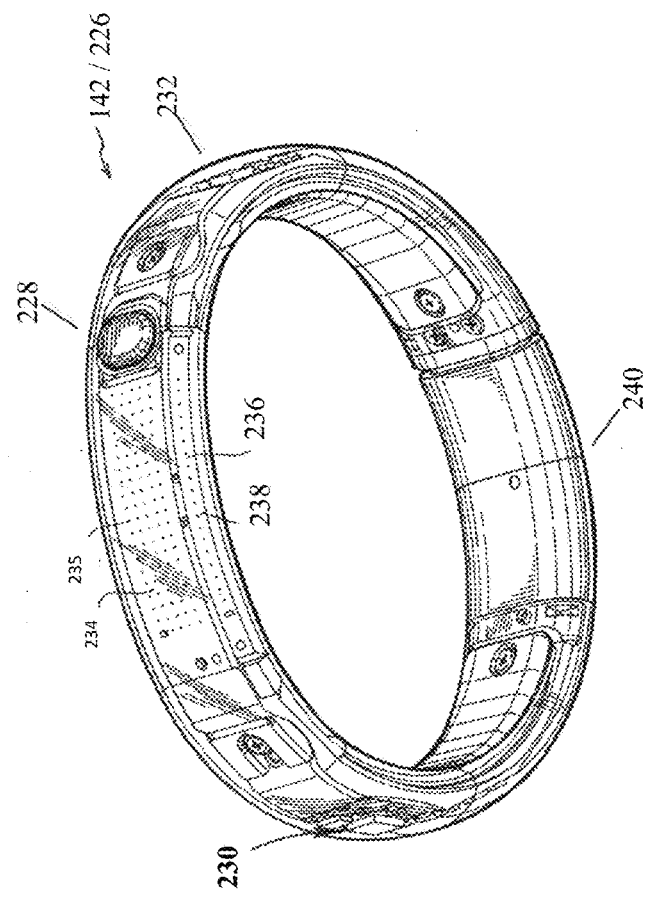
FIGS. 2A-B illustrate example sensor assemblies that may be worn by a user in accordance with example embodiments.
Figure 2A:
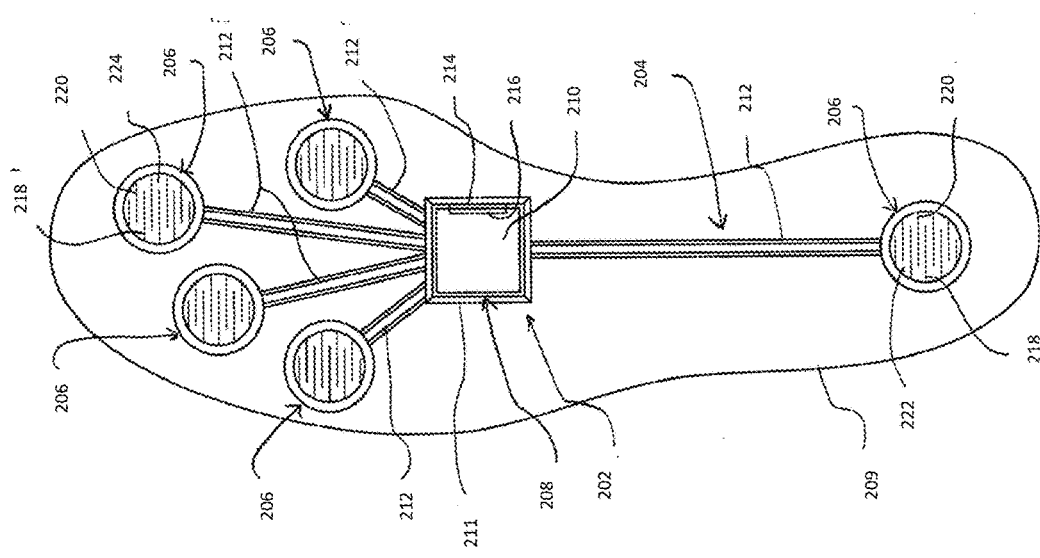

As shown in FIG. 2B, device 226 (which may be, or be a duplicative of or resemble sensory device 142 shown in FIG. 1A) may be configured to be worn by user 124, such as around a wrist, arm, ankle or the like. Device 226 may monitor movements of a user, including, e.g., athletic movements or other activity of user 124. For example, in one embodiment, device 226 may be activity monitor that measures, monitors, tracks or otherwise senses the user's activity (or inactivity) regardless of the user's proximity or interactions with computer 102. Device 226 may detect athletic movement or other activity (or inactivity) during user's 124 interactions with computer 102 and/or operate independently of computer 102. Device 226 may communicate directly or indirectly, wired or wirelessly, with network 132 and/or other devices, such as devices 138 and/or 140. Athletic data obtained from device 226 may be utilized in determinations conducted by computer 102, such as determinations relating to which exercise programs are presented to user 124. As used herein, athletic data means data regarding or relating to a user's activity (or inactivity). In one embodiment, device 226 may wirelessly interact with a remote website such as a site dedicated to fitness or health related subject matter, either directly or indirectly (e.g., via a mobile device, such as device 138 associated with user 124). In this or another embodiment, device 226 may interact with a mobile device, such as device 138, as to an application dedicated to fitness or health related subject matter. In these or other embodiments, device 226 may interest with both a mobile device as to an application as above, such as device 138, and a remote website, such as a site dedicated to fitness or health related subject matter, either directly or indirectly (e.g., via the mobile device, such as device 138). In some embodiments, at some predetermined time(s), the user may wish to transfer data from the device 226 to another location. For example, a user may wish to upload data from a portable device with a relatively smaller memory to a larger device with a larger quantity of memory. Communication between device 226 and other devices may be done wirelessly and/or through wired mechanisms.

As shown in FIG. 2B, device 226 may include an input mechanism, such as a button 228, to assist in operation of the device 226. The button 228 may be a depressible input operably connected to a controller 230 and/or any other electronic components, such as one or more elements of the type(s) discussed in relation to computer 102 shown in FIG. 1B. Controller 230 may be embedded or otherwise part of housing 232. Housing 232 may be formed of one or more materials, including elastomeric components and comprise one or more displays, such as display 234. The display may be considered an illuminable portion of the device 226. The display 234 may include a series of individual lighting elements or light members such as LED lights 234 in an exemplary embodiment. The LED lights may be formed in an array and operably connected to the controller 230. Device 226 may include an indicator system 236, which may also be considered a portion or component of the overall display 234. It is understood that the indicator system 236 can operate and illuminate in conjunction with the display 234 (which may have pixel member 235) or completely separate from the display 234. The indicator system 236 may also include a plurality of additional lighting elements or light members 238, which may also take the form of LED lights in an exemplary embodiment. In certain embodiments, indicator system 236 may provide a visual indication of goals, such as by illuminating a portion of lighting members 238 to represent accomplishment towards one or more goals.

A fastening mechanism 240 can be unlatched wherein the device 226 can be positioned around a wrist of the user 124 and the fastening mechanism 240 can be subsequently placed in a latched position. The user can wear the device 226 at all times if desired. In one embodiment, fastening mechanism 240 may comprise an interface, including but not limited to a USB port, for operative interaction with computer 102 and/or devices 138, 140, and/or recharging an internal power source.

In certain embodiments, device 226 may comprise a sensor assembly (not shown in FIG. 2B). The sensor assembly may comprise a plurality of different sensors. In an example embodiment, the sensor assembly may comprise or permit operative connection to an accelerometer (including in the form of a multi-axis accelerometer), a gyroscope, a location-determining device (e.g., GPS), light sensor, temperature sensor (including ambient temperature and/or body temperature), heart rate monitor, image-capturing sensor, moisture sensor and/or combinations thereof. Detected movements or parameters from device's 142 sensor(s), may include (or be used to form) a variety of different parameters, metrics or physiological characteristics including but not limited to speed, distance, steps taken, and energy expenditure such as calories, heart rate and sweat detection. Such parameters may also be expressed in terms of activity points or currency earned by the user based on the activity of the user. Examples of wrist-worn sensors that may be utilized in accordance with various embodiments are disclosed in U.S. patent application Ser. No. 13/287,064, filed on Nov. 1, 2011, the contents of which are incorporated herein in their entirety for any and all non-limiting purposes.

II. Illustrative Athletic Monitoring Methods

System 100 may prompt a user to perform one or more exercises, monitor user movement while performing the exercises, and provide the user with feedback based on their performance. In one embodiment, computer 102, image-capturing device 126, sensor 128, and display 136 may be implemented within the confines of a user's residence, although other locations, including schools, gyms and/or businesses are contemplated. Further, as discussed above, computer 102 may be a portable device, such as a cellular telephone, therefore, one or more aspects discussed herein may be conducted in almost any location.

A. Monitoring User Movements

Figure 3:
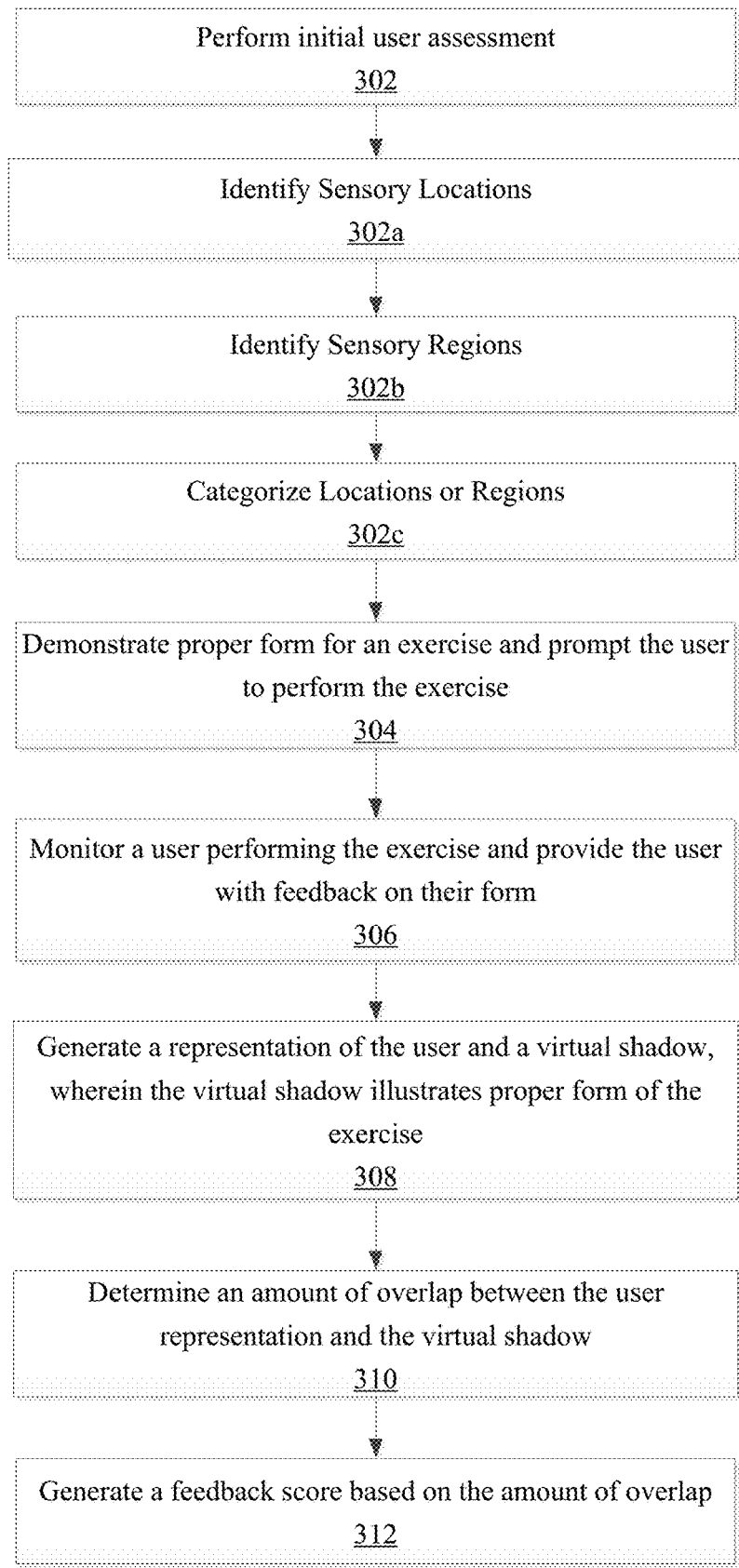
FIG. 3 illustrates an example flow diagram of a method for providing a user with feedback while exercising, in accordance with example embodiments.

While exercising, the system 100 may use one or more techniques to monitor user movement. FIG. 3 illustrates an example flow diagram of a method for providing a user with feedback while exercising, in accordance with one or more example embodiments. The method may be implemented by a computer, such as, for example, computer 102, device 138, 140, 142 and/or 144, and/or other apparatuses. The blocks shown in FIG. 3 may be rearranged, some blocks may be removed, additional blocks may be added, each block may be repeated one or more times, and the flow diagram may be repeated one or more times. The flow diagram may begin at block 302.

1. Perform User Assessment

In block 302, one or more embodiments may include performing an initial assessment of the user. A user, such as user 124, may be positioned in range of a sensor, such as in front of the image capturing device 126 and/or sensor 128, which may comprise an infrared transceiver. Display 136 may present a representation of user 124 that may be a "mirror-image" or depict a virtual avatar, such as a user avatar, that moves to correspond with user movement. Computer 102 may prompt the user to move into a certain region relative to the image capturing device 126 and/or relative to the sensor 128 so that the user is within frame and/or range. When properly positioned, the system 100 may process movement of the user. Although the term "initial" has been utilized, this assessment may occur each time the user initiates system 100, or upon predetermined (e.g., regular or random) times that the user initiates system 100, or upon passage of time (e.g., from first initiation or thereafter based on such occurrences in turn), or each time the user performs any one or more of some predetermined, user-selected, sequence, set or other movement, or for any other reason. Thus, references to assessments herein are not limited to a single assessment.

a. Identify Sensory Locations

The system 100 may process sensory data to identify user movement data. In one embodiment, sensory locations may be identified (see block 302*a*). For example, images of recorded video, such as from image-capturing device 126, may be utilized in an identification of user movement. For example, the user may stand a certain distance, which may or may not be predefined, from the image-capturing device 126, and computer 102 may process the images to identify the user 124 within the video, for example, using disparity mapping techniques. In an example, the image capturing device 126 may be a stereo camera having two or more lenses that are spatially offset from one another and that simultaneously capture two or more images of the user. Computer 102 may process the two or more images taken at a same time instant to generate a disparity map for determining a location of certain parts of the user's body in each image (or at least some of the images) in the video using a coordinate system (e.g., Cartesian coordinates). The disparity map may indicate a difference between an image taken by each of the offset lenses.

Figure 4:
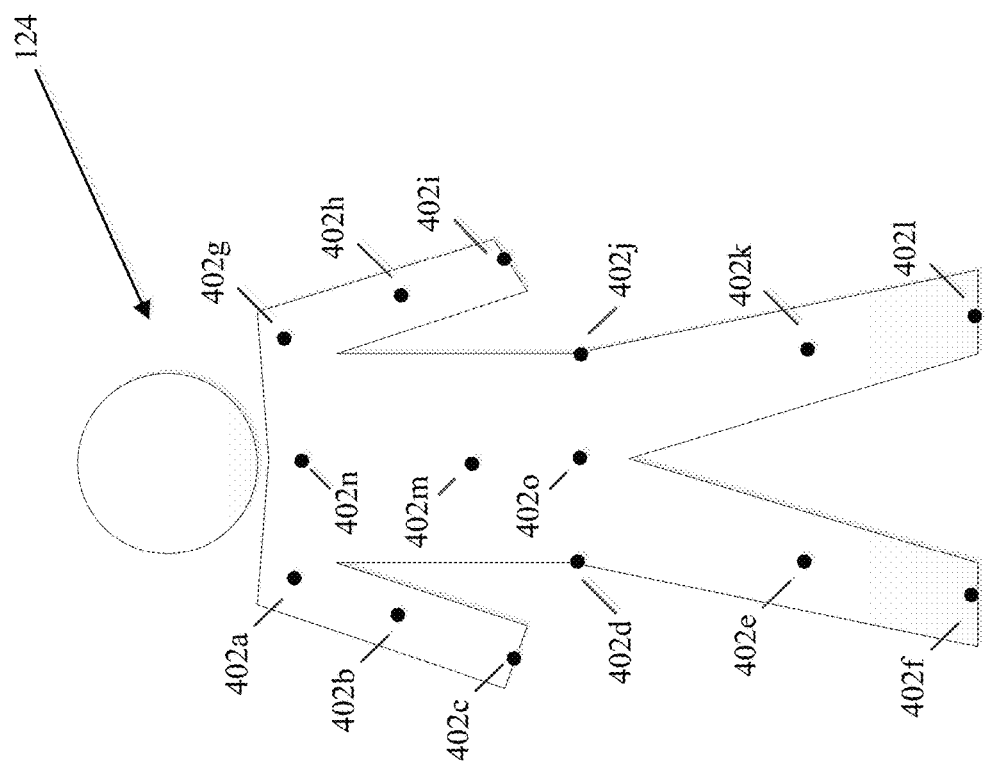
FIG. 4 illustrates example points on a user's body to monitor in accordance with example embodiments.

In a second example, one or more sensors may be located on or proximate to the user's 124 body at various locations or wear a suit having sensors situated at various locations. Yet, in other embodiments, sensor locations may be determined from other sensory devices, such as devices 138, 140, 142 and/or 144. With reference to FIG. 4, sensors may be placed (or associated with, such as with image-capturing device 126) body movement regions, such as joints (e.g., ankles, elbows, shoulders, etc.) or at other locations of interest on the user's 124 body. Example sensory locations are denoted in FIG. 4 by locations 402a-402o. In this regard, sensors may be physical sensors located on/in a user's clothing, yet in other embodiments, sensor locations 402a-402o may be based upon identification of relationships between two moving body parts. For example, sensor location 402a may be determined by identifying motions of user 124 with an image-capturing device, such as image-capturing device 126. Thus, in certain embodiments, a sensor may not physically be located at a specific location (such as sensor locations 402a-402o), but is configured to sense properties of that location, such as with image-capturing device 126. In this regard, the overall shape or portion of a user's body may permit identification of certain body parts. Regardless of whether an image-capturing device, such as camera 126, is utilized and/or a physical sensor located on the user 124, such as sensors within or separate from one or more of device(s) 138, 140, 142, 144 are utilized, the sensors may sense a current location of a body part and/or track movement of the body part. In one embodiment, location 402m may be utilized in a determination of the user's center of gravity (a.k.a, center of mass). For example, relationships between location 402a and location(s) 402f/402l with respect to one or more of location(s) 402m-402o may be utilized to determine if a user's center of gravity has been elevated along the vertical axis (such as during a jump) or if a user is attempting to "fake" a jump by bending and flexing their knees. In one embodiment, sensor location 402n may be located at about the sternum of user 124. Likewise, sensor location 402o may be located approximate to the naval of user 124. In certain embodiments, data from sensor locations 402m-402o may be utilized (alone or in combination with other data) to determine the center of gravity for user 124. In further embodiments, relationships between multiple several sensor locations, such as sensors 402m-402o, may be utilized in determining orientation of the user 124 and/or rotational forces, such as twisting of user's 124 torso. Further, one or more locations, such as location(s), may be utilized to as a center of moment location. For example, in one embodiment, one or more of location(s) 402m-402o may serve as a point for a center of moment location of user 124. In another embodiment, one or more locations may serve as a center of moment of specific body parts or regions.

In certain embodiments, a time stamp to the data collected (such as collected part of block 302 in FIG. 3) indicating a specific time when a body part was at a certain location. Sensor data may be received at computer 102 (or other device) via wireless or wired transmission. A computer, such as computer 102 and/or devices 138, 140, 142, 144 may process the time stamps to determine the locations of the body parts using a coordinate system (e.g., Cartesian coordinates) within each (or at least some) of the images in the video. Data received from image-capturing device 126 may be corrected, modified, and/or combined with data received from one or more other devices 138, 140, 142 and 144.

In a third example, computer 102 may use infrared pattern recognition to detect user movement and locations of body parts of the user 124. For example, the sensor 128 may include an infrared transceiver, which may be part of image-capturing device 126, or another device, that may emit an infrared signal to illuminate the user's 124 body using infrared signals. The infrared transceiver 128 may capture a reflection of the infrared signal from the body of user 124. Based on the reflection, computer 102 may identify a location of certain parts of the user's body using a coordinate system (e.g., Cartesian coordinates) at particular instances in time. Which and how body parts are identified may be predetermined based on a type of exercise a user is requested to perform.

Figure 5:
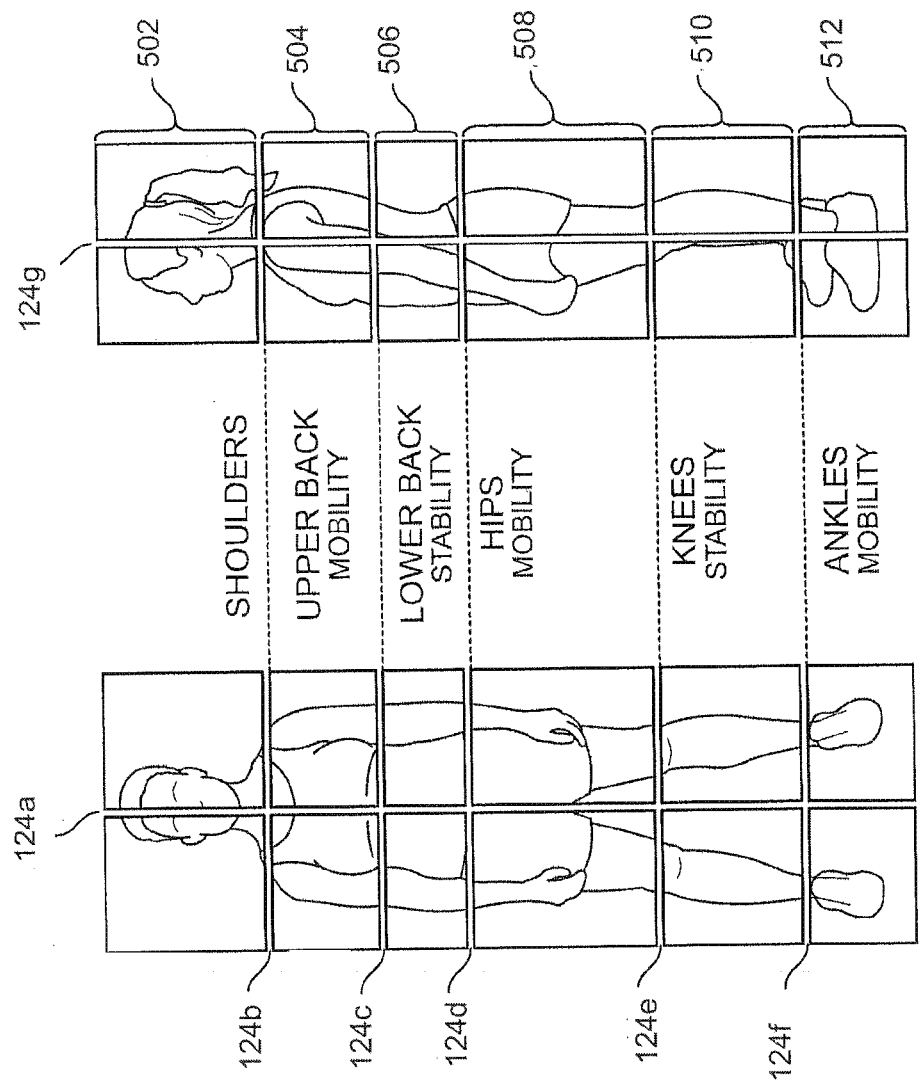
FIG. 5 illustrates an example posture assessment in accordance with example embodiments.

As part of a workout routine, computer 102 may make an initial postural assessment of the user 124 as part of the initial user assessment in block 302 of FIG. 3. With reference to FIG. 5, computer 102 may analyze front and side images of a user 124 to determine a location of one or more of a user's shoulders, upper back, lower back, hips, knees, and ankles. On-body sensors and/or infrared techniques may also be used, either alone or in conjunction with image-capturing device 126, to determine the locations of various body parts for the postural assessment. For example, computer 102 may determine assessment lines 124a-g to determine the locations of a various points on a user's body, such as, for example, ankles, knees, hips, upper back, lower back, and shoulders.

b. Identify Sensory Regions

In further embodiments, system 100 may identify sensor regions (see, e.g. block 302b). In one embodiment, assessments lines 124a-g may be utilized to divide the user's body into regions. For example, lines 124b-f may be horizontal axes. For example, a "shoulders" region 502 may correlate to a body portion having a lower boundary around the user's shoulders (see line 124b), region 504 may correlate to the body portion between the shoulders (line 124b) and about half the distance to the hips (see line 124c) and thus be an "upper back" region, and region 506 may span the area between line 124c to the hips (see line 124d) to comprise a "lower back region." Similarly, region 508 may span the area between the "hips" (line 124d) and the "knees" (see line 124e), region 510 may span between lines 124e and 124f and region 512 (see "ankles") may have an upper boundary around line 124f Regions 502-512 may be further divided, such as into quadrants, such as by using axes 124a and 124g c. Categorize Locations or Regions Regardless of whether specific points (e.g., locations shown in FIG. 4) and/or regions (e.g. regions shown in FIG. 5), body parts or regions that are not proximate to each other may nonetheless be categorized into the same movement category (see, e.g. block 302c). For example, as shown in FIG. 5, the "upper back", "hips", and "ankles" regions 504, 508, 512 may be categorized as belonging to a "mobility" category. In another embodiment, the "lower back" and "knees" regions 506, 510 may be categorized as belonging to a "stability" category. The categorizations are merely examples, and in other embodiments, a location or region may belong to multiple categories. For example, a "center of gravity" region may be formed from regions 504 and 506. In one embodiment, a "center of gravity" may comprise portions of regions 504 and 506. IN another embodiment, a "center of moment" category may be provided, either independently, or alternatively, as comprising a portion of at least another category. In one embodiment, a single location may be weighted in two or more categories, such as being 10% weighted in a "stability" category and 90% weighted in a "mobility" category.

Computer 102 may also process the image to determine a color of clothing of the user or other distinguishing features to differentiate the user from their surroundings. After processing, computer 102 may identify a location of multiple points on the user's body and track locations of those points, such as locations 402 in FIG. 4. Computer 102 may also prompt the user to answer questions to supplement the postural assessment, such as, for example, age, weight, etc.

2. Providing Form

With reference again to FIG. 3, in block 304, one or more embodiments may include demonstrating proper form for an exercise and prompting the user to perform the exercise. For example, after or in addition to the initial postural assessment, computer 102 may cause the display 136 to present a virtual trainer demonstrating an exercise to instruct the user on proper form.

Figure 6:
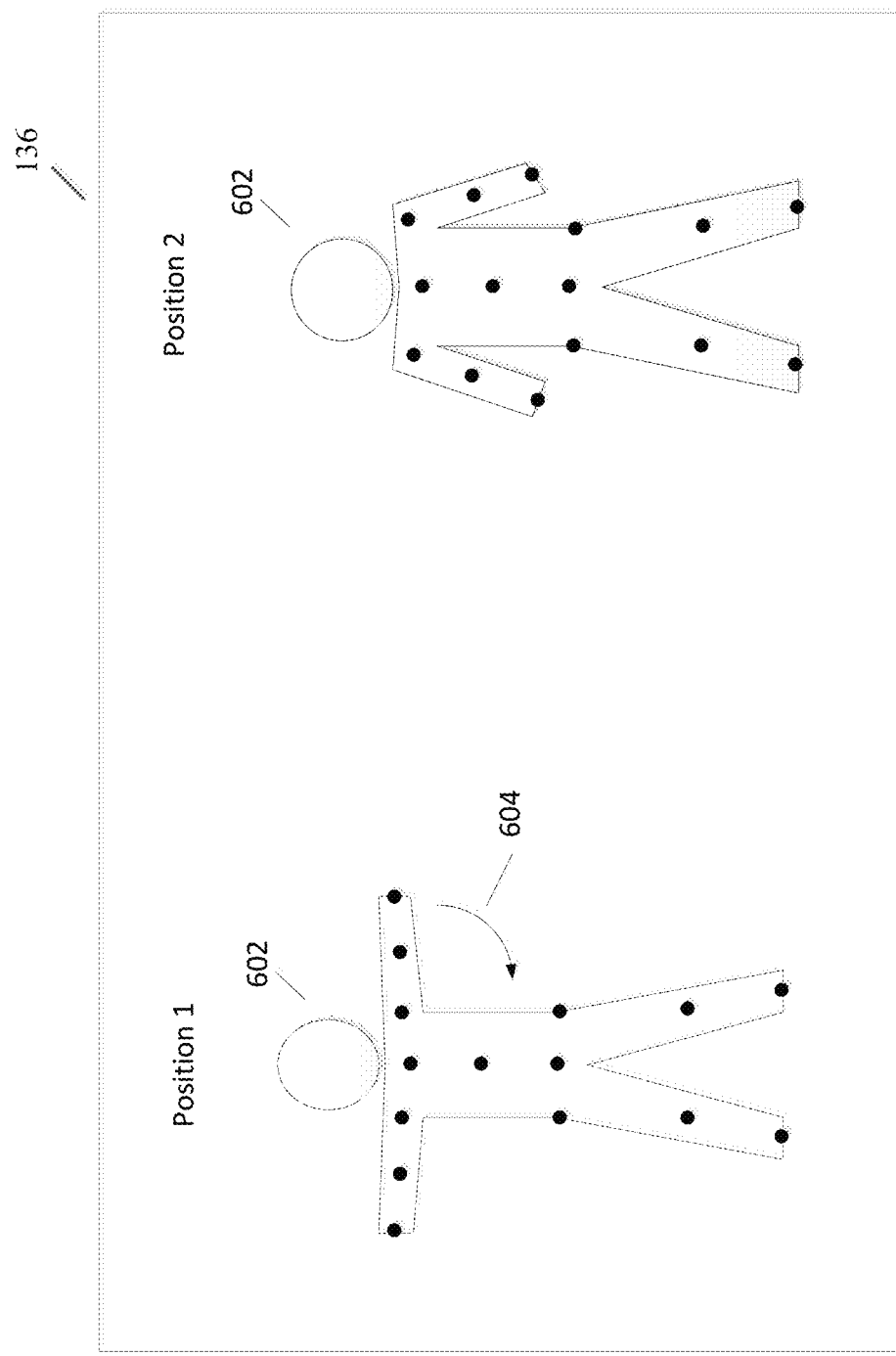
FIGS. 6-7 illustrate example displays of a virtual trainer instructing a user on how to perform an exercise in accordance with example embodiments.
Figure 7:
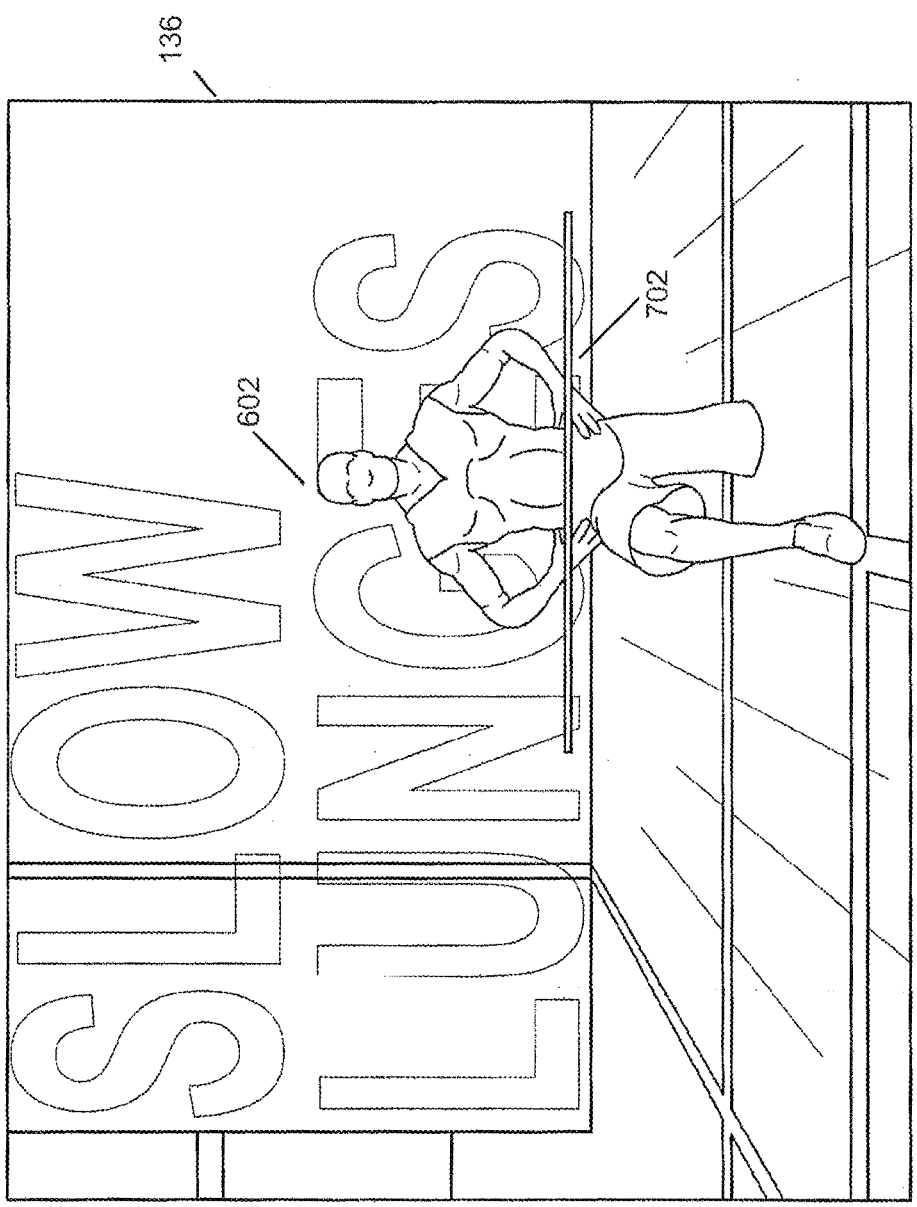

FIGS. 6-7 illustrate example displays of a virtual trainer 602 performing an exercise in accordance with example embodiments. With reference to FIG. 6, the display 136 may present a virtual trainer 602 at multiple positions as well as an arrow 604 instructing a user in which direction to move. With reference to FIG. 7, the display 136 may present an animation of the virtual trainer 602 demonstrating proper form for performing a repetition of an exercise (e.g., a slow lunge). In addition to or instead of a virtual trainer 602, the display 136 may present a depiction and/or an actual video of a real person demonstrating proper form for an exercise.

Form guidance information 702 may be presented on the virtual trainer 602 when demonstrating an exercise. Form guidance information 702 may be a straight line, an angle between lines, or other information to guide the user about proper form for an exercise. In FIG. 7, for instance, form guidance information 702 is a straight line across a user's hip bones instructing the user to keep their hips level relative to the floor. Form guidance information may be provided through feedback mechanisms that do not include graphical or textual data overlaid on an avatar, such as virtual trainer 602. In this regard, form guidance information may include audio or tactile information. For example, voices or sounds may provide an indication of how straight a user's hips are (or are not). In another embodiment, a signal may be provided to a device, such as sensor device(s) 138, 140, 142 and/or 144 to provide vibrational output configured to be felt by user 124 to provide guidance. For example, a vibration may be provided to the sensor device 138 upon determining that the user's hips are not straight.

B. Feedback

Figure 8:
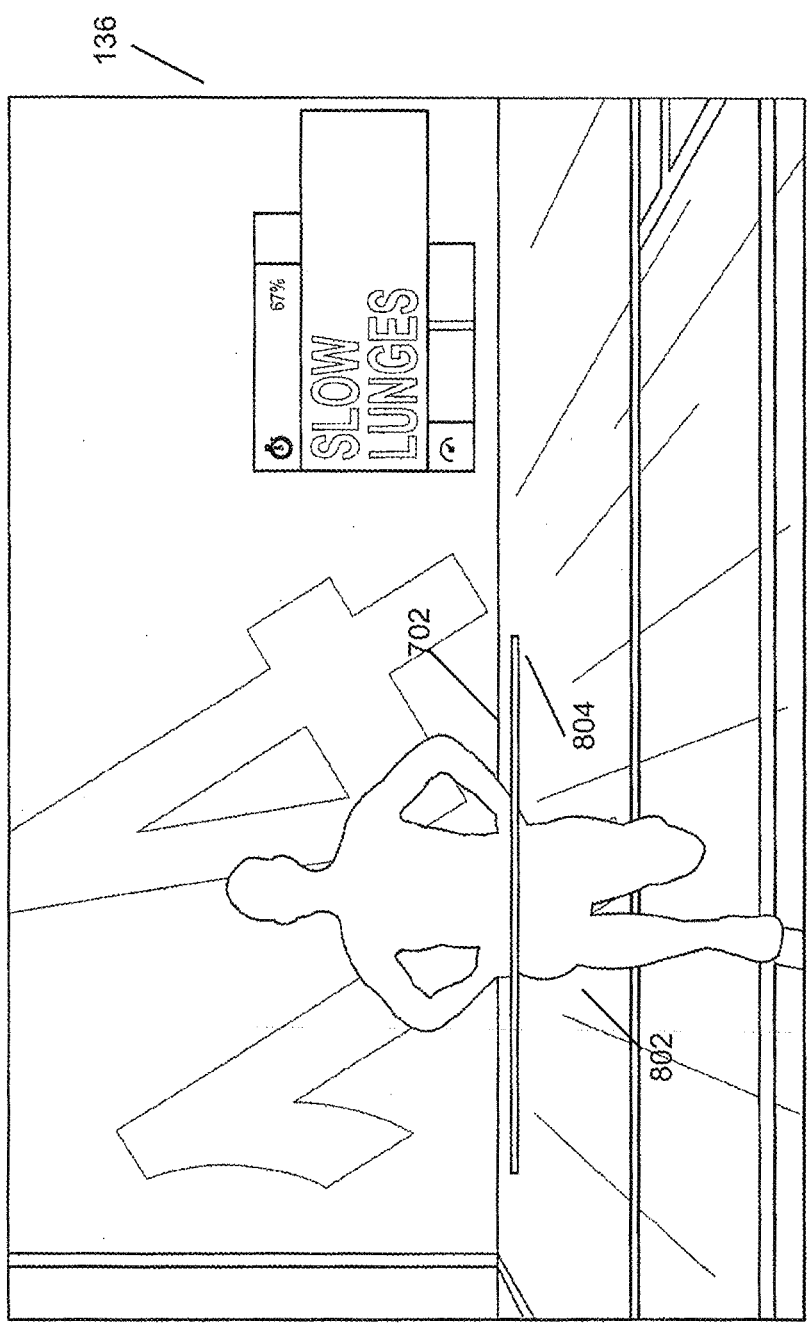

With reference again to FIG. 3, in block 306, one or more embodiments may comprise monitoring a user performing an exercise and providing the user with feedback on their form. While performing an exercise, computer 102 may cause a display, such as display 136, to present a user representation with real-time feedback. FIG. 8 illustrates an example display of a user representation performing an exercise in accordance with example embodiments. While user 124 is performing movements, computer 102 may create a user representation for display by the display 136. The computer may create the user representation based on one or more of processing some or all images of video captured by image capturing device 126, processing data received from the sensor 128, and processing data received from sensors 138, 140, 142, and 144. The user representation may be, for example, video of the user, or a user avatar 802 created based on image and/or sensor data, including infrared data.

1. Guide Information

To assist the user 124, display 136 may also present form guidance information 702 on user avatar 802, as well as current form information 804 for the user. Current form information 804 may be a measurement of a user's current form of interest in a particular exercise. Current form information 804 may be a straight line between particular body parts, an angle between certain body parts, curvature of a body part, or other information being monitored for a particular exercise. For example, as seen in FIG. 8, current form information 804 may be a straight line between a user's hips to indicate if one hip sags relative to the other (e.g., to indicate whether a straight line between the user's hips is parallel with the floor). Also, the user may place sensors on their body at their hip bones, or computer 102 may estimate a location of a user's hip bones based on detected infrared information. A color of the current form information 804 may vary based on how well the user's form corresponds to desired form. For example, green may indicate less than a 5 degree angle between lines of the form guidance information 702 and the current form information 804, yellow may indicate a 5 degree to 15 degree angle between lines of the form guidance information 702 and the current form information 804, and red may indicate greater than a 15 degree angle between lines of the form guidance information 702 and the current form information 804.

To further aid a user in having proper form, computer 102 may also process captured data, such as from the images, infrared data, and/or sensor data, to determine a relationship between certain body parts. These relationships may include an angle of one body part relative to another. For example, when the user is doing a squat, computer 102 may compare an angle formed between a user's torso and thigh. In another example, computer 102 may compare a location of a user's shoulder relative to their elbow and hand during a push up. In another example, computer 102 may compare shoulders and hips to determine relative rotation there between, and/or either or both shoulder and hips relative to one or more feet to determine relative rotation there between or there among, and/or absolute rotation of either the hips or shoulders. Angles, rotations, and other relationships between or among any one or more desired body part(s) may be monitored and analyzed. Angles, rotations, and other relationships between or among a reference point (e.g., off body) and any one or more desired body part(s) may be monitored and analyzed.

2. Comparison of Data

Computer 102 may compare the captured data to desired data for each exercise to monitor the user's form while performing an exercise. The desired data may include multiple comparison points throughout an exercise, and/or locations of various body parts during the exercise. For example, a push up may be divided into four events: (1) the lowest point where the user's chest is nearest to the ground or other reference point and/or their arms are bent at a maximum bend; (2) a highest point where the user's chest is farthest from the ground and/or their arms are straightened (e.g., a maximum straightness); (3) an upward event where the user transitions from the lowest point to the highest point; and (4) a downward event where the user transitions from the highest point to the lowest point.

The desired data may specify comparison points for each of these events focusing on certain body parts. For example, at each comparison point during a pushup, computer 102 may monitor the spacing of the user's hands, the straightness of the user's back, a location of the user's head relative to their torso, the spacing of the user's feet relative to one another, or other aspects. The desired data may specify desired locations for each body part being monitored during comparison points for an exercise, as well as permitted variations from the desired locations. If the user's body part varies beyond what is permitted, computer 102 may provide the user with feedback identifying the body part and a correction to the user's form (e.g., back is arched, and not straight, during a pushup).

Computer 102 may also score the user's performance of an exercise. Scoring may be based on the user's form, how quickly the user was able to complete the exercise (e.g., 20 pushups in 60 seconds), a number of repetitions the user completed, the amount of weight the user used during an exercise, or other exercise metrics. In additional to processing the images, sensor data, and infrared data, computer 102 may receive data from other sources. For example, the user may run a predetermined distance as measured by a sensor attached to the user (e.g., sensor in a shoe) or global positioning system (GPS) device and may upload the data to computer 102. Computer 102 may process the data to provide the user with feedback. Computer 102 may also provide feedback based on analyzing a user from different viewpoints.

3. Representations

Figure 9:
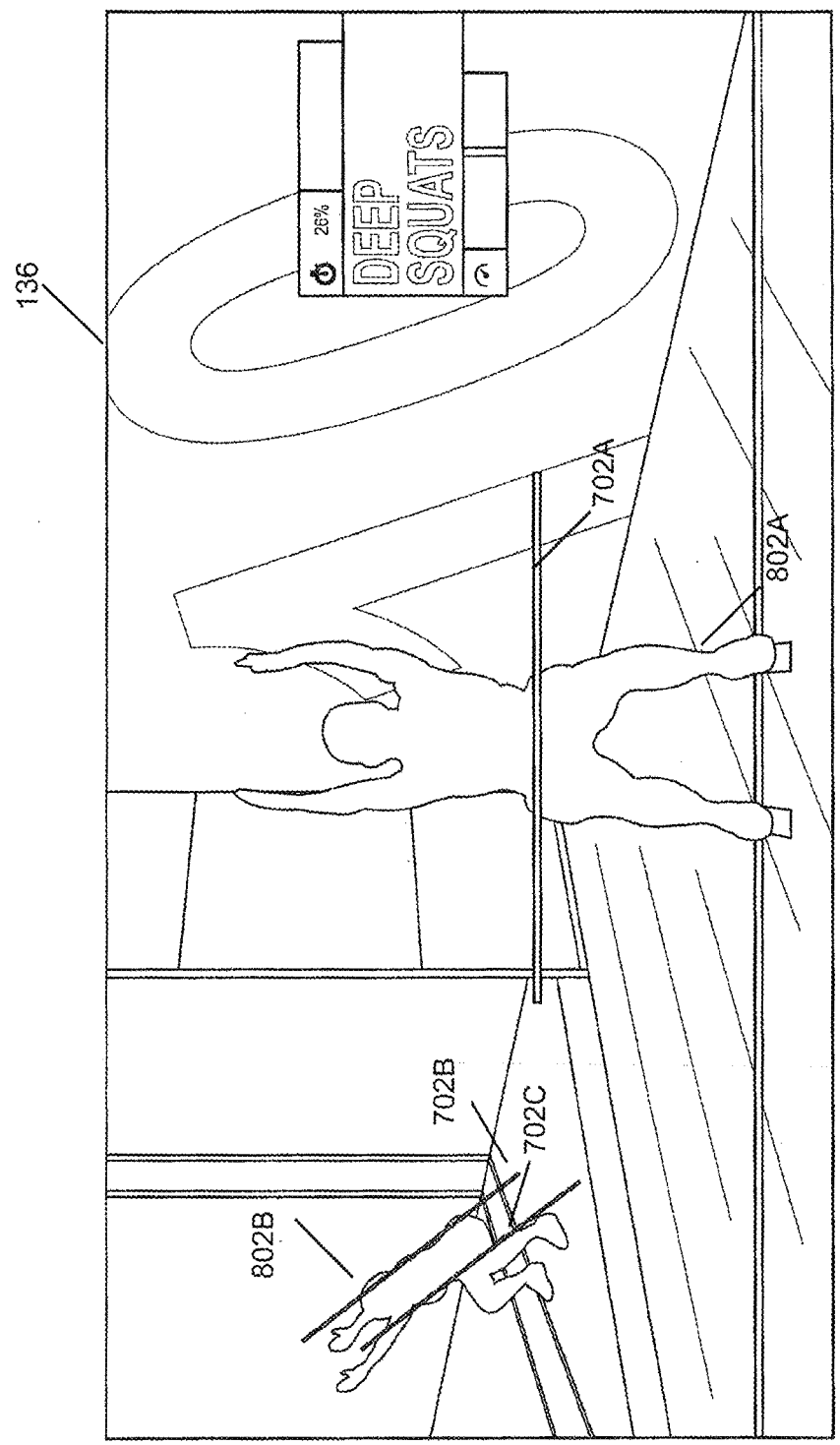

FIG. 9 illustrates an example display of multiple user avatars from different viewpoints performing an exercise in accordance with example embodiments. In an example, the system 100 of FIG. 1 may include more than one image capturing device 126 and may capture video from different perspectives. Yet, in other embodiments, data for different angles may be derived from one or more sources. For example, the image capturing device 126 may be positioned at any desired angle relative to a user performing an exercise, such as, for example, at least one of a front view, left side view, a right side view, and a back view of a user. In another example, the system 100 may include more than one infrared device 128 to capture infrared reflections of the user 124 from different perspective. Also, the system 100 may include both an image capturing device 126 and an infrared transceiver 128 (or more than either one or both) positioned at different/various locations.

Computer 102 may process some or all images and/or infrared data to create a first user avatar 802A and a second user avatar 802B for display by the display 136. In this manner, display 136 may present a user's form from multiple angles for the user to observe. Further, form guidance information 702A-C may be added to each of the user avatars 802A-B to aid the user in obtaining proper form.

FIGS. 10A-B illustrate example displays depicting form feedback on a user avatar in accordance with example embodiments. When exercising, display 136 may present multiple virtual targets 1002A-C on which the user is instructed to place a hand, foot, or other part of their body. For example, FIG. 10A depicts virtual target 1002A for a user's foot, virtual target 1002B for a user's other foot, and virtual target 1002C for a user's hands. The virtual targets 1002 may be used to aid a user in having proper form. Computer 102 may process video, sensor data, or infrared data for a user to determine if the user has placed the proper body part in the desired virtual target 1002 during performance of an exercise. If so, computer 102 may cause the display 136 to highlight each of the targets 1002 in a certain color (e.g., green) and/or play an audible sound. In one embodiment, a range of colors may be displayed based upon the performance of the user. Ranges of coloration may be based upon performance thresholds. For example, a green coloration may be utilized in a user is above a 90% threshold, an orange coloration is utilized if the user is between a 89%-70% threshold, and a red coloration may be utilized if the user's performance falls below a 70% threshold. Similarly, different sounds may be utilized to provide feedback to the user. If not, computer 102 may highlight each missed target 1002 and/or play an audible sound, and provide a suggestion to correct the user's form. For example, computer 102 may determine that a user's knees are bent resulting in the user missing targets (in whole or in part) 1002B-C. Computer 102 may cause display 136 to display user avatar 802 highlighting the knees and/or any other problem area (e.g., different color, encircle one or more body parts, inset picture with enlarged view of problem area, etc.). Display 136 may display an instruction 1006 to correct the user's form (e.g., straighten knees).

4. Shadows

Referring briefly again to FIG. 3, in block 308, one or more embodiments may include generating a representation of the user and a virtual shadow, wherein the virtual shadow illustrates proper form of the exercise. The example embodiments also may be used to display a virtual shadow relative to the user avatar 802. The virtual shadow may be used for one or more of demonstrating proper form, presenting a user's (or another individual's) previously recorded performance of an exercise relative to a user's current performance, providing real-time feedback to a user while exercising, facilitating social interaction and/or competition among a plurality of individuals, and providing post-workout feedback to a user on their form, as described in further detail below.

As provided in certain examples below, a shadow may be directly or partially overlaid with an avatar. In other embodiments, however, the shadow may not overlap an avatar at all. For example, in certain embodiments, a shadow may be in the form of a virtual trainer. Although illustrative embodiments disclosed herein relate to displaying the shadow to the user, such as during the user's performance of an athletic activity, other embodiments may not display a visual depiction of a shadow to a user 124. In certain embodiments, data corresponding to a dimensional virtual shadow may be utilized without actually displaying a visual depiction of a shadow to a user. This may be advantageous in implementations in which it is undesirable to provide an immediate indication of visual performance measurements to the user. In certain embodiments, audio and/or video cues may provide feedback to the user indicative of their performance relating to a shadow—either independently of or in combination with the shadow.

FIG. 11 illustrates an example user avatar having a virtual shadow 1102 to permit a user, such as user 124 shown in FIG. 1, to compete against themselves or others, in accordance with example embodiments. Initially, computer 102 may monitor a user performing an exercise using the image capturing device 126, sensor 128, and/or sensory devices 138, 140, 142 and/or 144. Based on the collected data, computer 102 may create a user representation, such as a user avatar 802, as well as a virtual shadow 1102. The shadow 1102, for example, may be a more transparent version of the user avatar 802, a user avatar 802 presented in a different color, a user avatar 802 presented having a pattern (e.g., grid, cross hatching, etc.), etc., an avatar 802 having a contrasting structure (e.g., composed of spheres, wafers, blocks), etc. Any visual distinctions may be utilized to differentiate avatar 802 from shadow 1102.

a. User vs. User

In an example, the virtual shadow 1102 may be displayed with the appearance that a user, such as user 124, is competing against him or herself. For example, computer 102 (or any other electronic device) may store a user avatar 802 while the user 124 performs an exercise. Later, computer 102 may prompt the user if they would like to compete against their earlier performance of the exercise. In that case, system 100 may generate a virtual shadow 1102 based on the user avatar 802 generated from the most recent or a selected earlier completed exercise session. Self-competition may permit a user to view their improvement over time, including, as examples, the latest improvement or improvement over a (e.g., user-selected) time period or improvement from a beginning.

Figure 12:
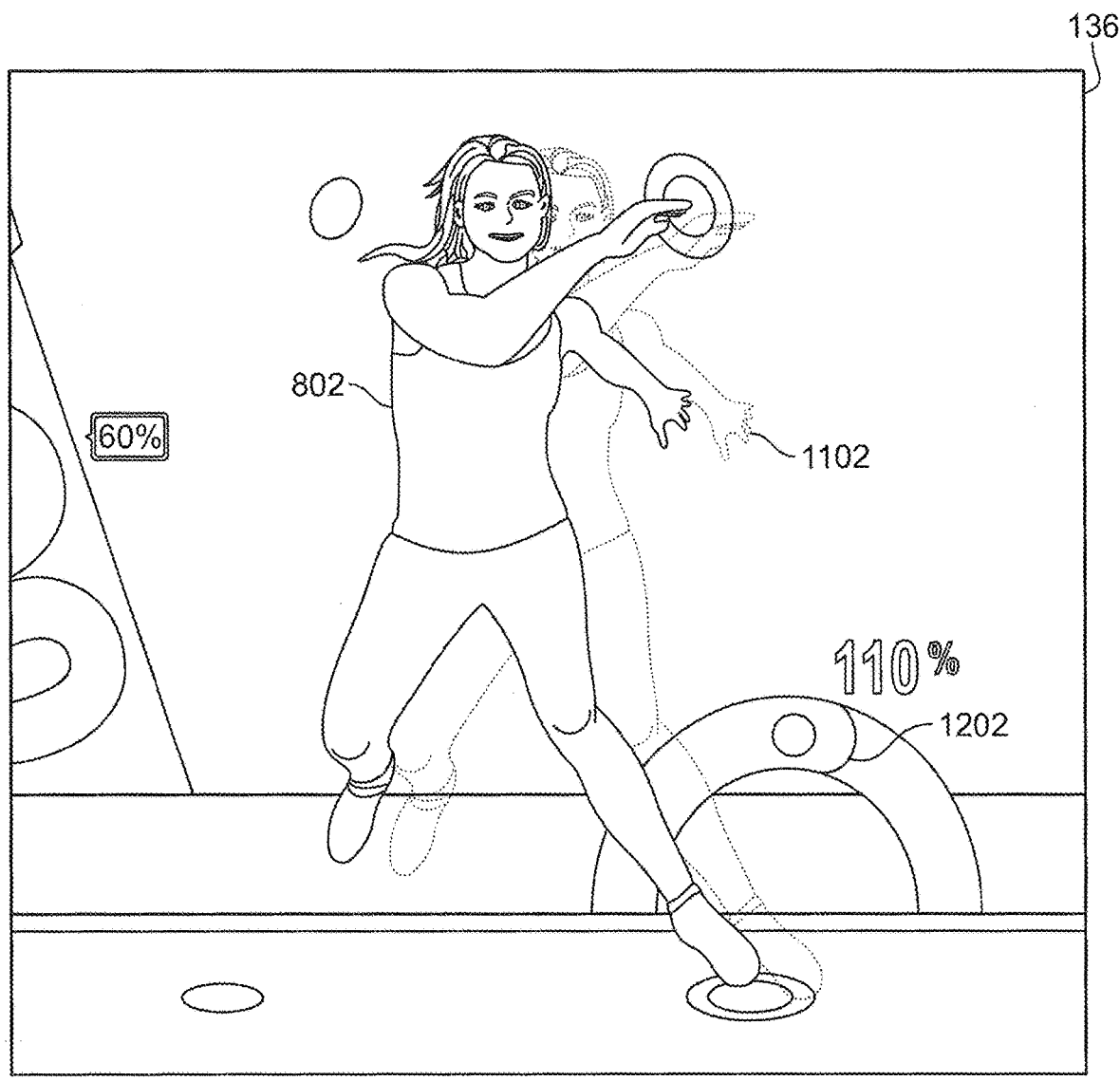
Figure 13B:
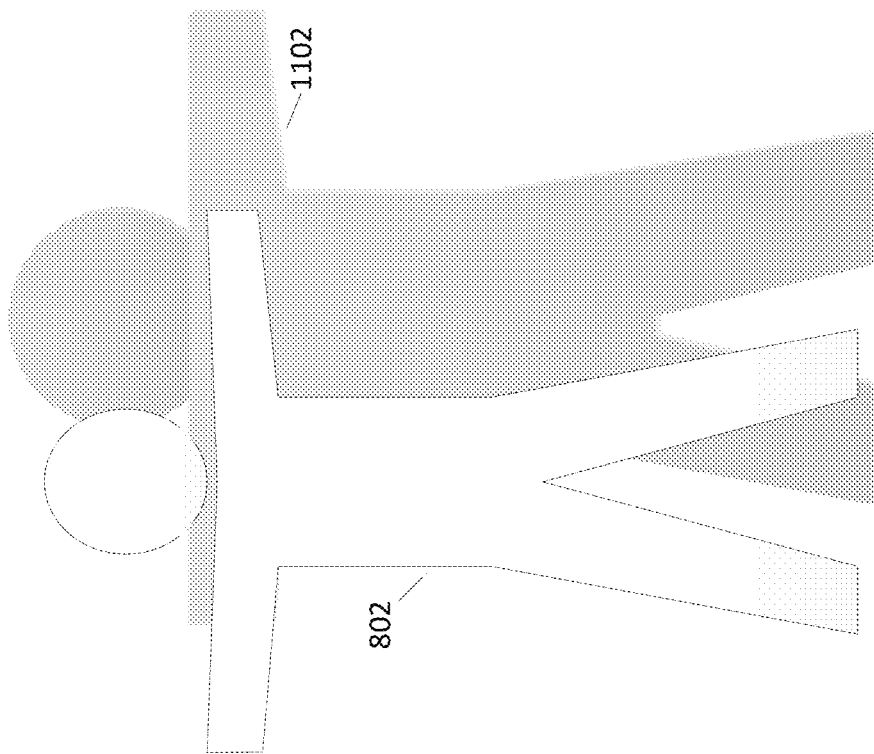
FIGS. 13A-13B illustrate example locations of virtual shadows for a user avatar in accordance with example embodiments.

When competing against him or herself, computer 102 may generate a new user avatar 802 as the user performs an exercise for simultaneous display with the virtual shadow 1102. The new user avatar 802 may be displayed overtop of or directly behind the shadow, as seen in for example, FIGS. 11 and 13A. Alternatively, the display 136 may present a shadow 1102 offset from the new user avatar 802, for example, as shown in FIGS. 12 and 13B. Computer 102 may synchronize the start times such that the user avatar 802 appears to be competing against the virtual shadow 1102. When an exercise is complete, computer 102 may inform the user 124 of the winner, and provide side by side statistics of the current performance relative to the virtual shadow 1102. An example of which is shown by statistics 1104 shown in FIG. 11.

The display 136 may also present one or more performance level indicators 1202 to indicate a user's performance metrics, as depicted in FIG. 12. Performance level indicators may be displayed instead of a shadow. Yet, in other embodiments, indicators may be displayed in conjunction with a shadow. Example metrics may include speed, quickness, power, dimensions (e.g., distance stepped or dipped, height jumped, rotation of hips or shoulders), reaction time, agility, flexibility, acceleration, heart rate, temperature (e.g., overheating), blood oxygen content, or other physical or physiological metrics. A performance level indicator 1202 may be depicted as, for example, a gauge, a speedometer, a bar-type indictor, percentage indicator, etc.

b. User v. Another User

In an example, a virtual shadow 1102 may be displayed with the appearance that a user, such as user 124, is competing against another user. In one embodiment, user 124 may be located at a first physical location, such as their home, and a second user may be located at a second physical location, such as a gym, dwelling, school, or even exercising outside, such as running through a city. Despite being at different physical locations, users may still compete and/or collectively engage in athletic activities. In one embodiment, each of a plurality of users may engage in a competition in substantially real-time. Yet, in other embodiments, a first user may conduct a predefined series of activities or routines and data from that first user's performance may be utilized in a later conducted competition. In one embodiment, two or more users may engage in a "side-by-side" competition. For example, computer 102 (or any other electronic device) may generate or store a user avatar 802 while a first user 124 performs an exercise. The same computer 102 and/or another computer, such as an electronic device that is in operative communication with network 132, may generate and/or store a second avatar representing the second user. Both of these avatars may be displayed on a single display device, such as display 136 at the location of user 124 (and/or at the location of the second user). Thus, user 124 may see both avatars. Each user's avatar may be displayed with their own shadow during the performance of any athletic activities. In certain implementations, the shadows may represent an ideal form for the respective user. Examples of using shadows to represent forms are provided below in the following subsection. In further embodiments, users may be "handicapped" by utilizing variable shadow properties. Shadows may be generated based upon past performance in one or more activities, such as the activity being performed in competition or upon an assessment of a person's respective capabilities (e.g., current fitness level). Therefore, although two users may be competing against each other, one or both shadows other than those representing ideal form may be utilized so as to require a first user to have relatively better form and/or fitness parameters than a second user (e.g., the first user's virtual shadow may represent ideal form, while the second user's virtual shadow is less than ideal, such as in proportion with the relative fitness of the two users).

In other embodiments, users may compete with another user's shadow. For example, a first user, such as user 124 may have had a great workout and want to challenge a second user to see how they perform or stack up against the first user's workout. A shadow representing the first user's workout may be transmitted to permit the second user to compete against the first user's performance. In one embodiment, a virtual avatar 802 of the second user may be displayed on display 136. A virtual shadow 1102 may be generated based upon the workout of the first user 124. System 100 may synchronize the start times such that the user avatar 802 appears to be competing against the virtual shadow 1102. When an exercise is complete, computer 102 may inform either user of the winner. System 100 may also provide side by side statistics of the second user's current performance relative to the virtual shadow 1102 of the first user 124. Competing with other users' shadow(s) 1102 may be performed in a real-time environment as well as permitting shadows 1102 from previous athletic activities to be utilized.

c. Proper Form

Figure 13A:
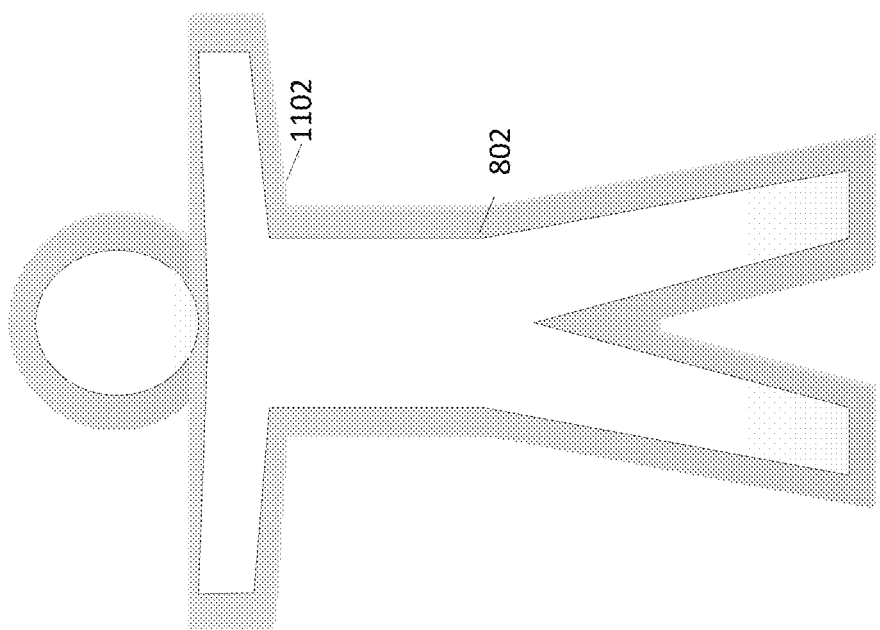

In accordance with certain embodiments, computer 102 (or any other electronic device) may also use the shadow 1102 to provide feedback to a user on proper form. To aid a user with their form, virtual shadow 1102 may be used to present proper form to a user while the user 124 is performing the exercise. For instance, the virtual shadow 1102 may be created based on capturing data from a professional athlete or trainer demonstrating proper form for an exercise. While performing repetitions of an exercise, computer 102 may cause the display 136 to present the virtual shadow 1102 with proper exercise form relative to the user avatar 802. For instance, the virtual shadow 1102 may be depicted overtop of the user avatar 802, as shown in FIG. 13A, or offset from the user avatar 802, for example as shown in FIG. 13B. In an example, the virtual shadow 1102 may be an animation moved at the same pace as the user performing an exercise. In one embodiment, computer 102 is configured to alter the pace of an animation based on the user's performance of the exercise.

d. Shadow Overlap

Further embodiments may include determining an amount of overlap between the user representation and the virtual shadow (see block 310 of FIG. 3). In an example, computer 102 (or any other electronic device) may monitor and/or adjust how the user avatar 802 overlaps with the virtual shadow 1102 to provide the user with real-time feedback. For example, computer 102 may define one or more overlap thresholds. In one embodiment, computer 102 may monitor the overlap of shadow 1102 and avatar 802. In one embodiment, system 100 may determine that a user's form is good if there is at least a first predetermined threshold overlap (e.g., 95% or higher) between the virtual shadow 1102 and the user avatar 802, the user's form is acceptable if there is at least a second predetermined threshold overlap (e.g., between 85% and 95%), and that the user's form is improper if there is less than the second predetermined threshold overlap (e.g., less than 85%).

Figure 14:
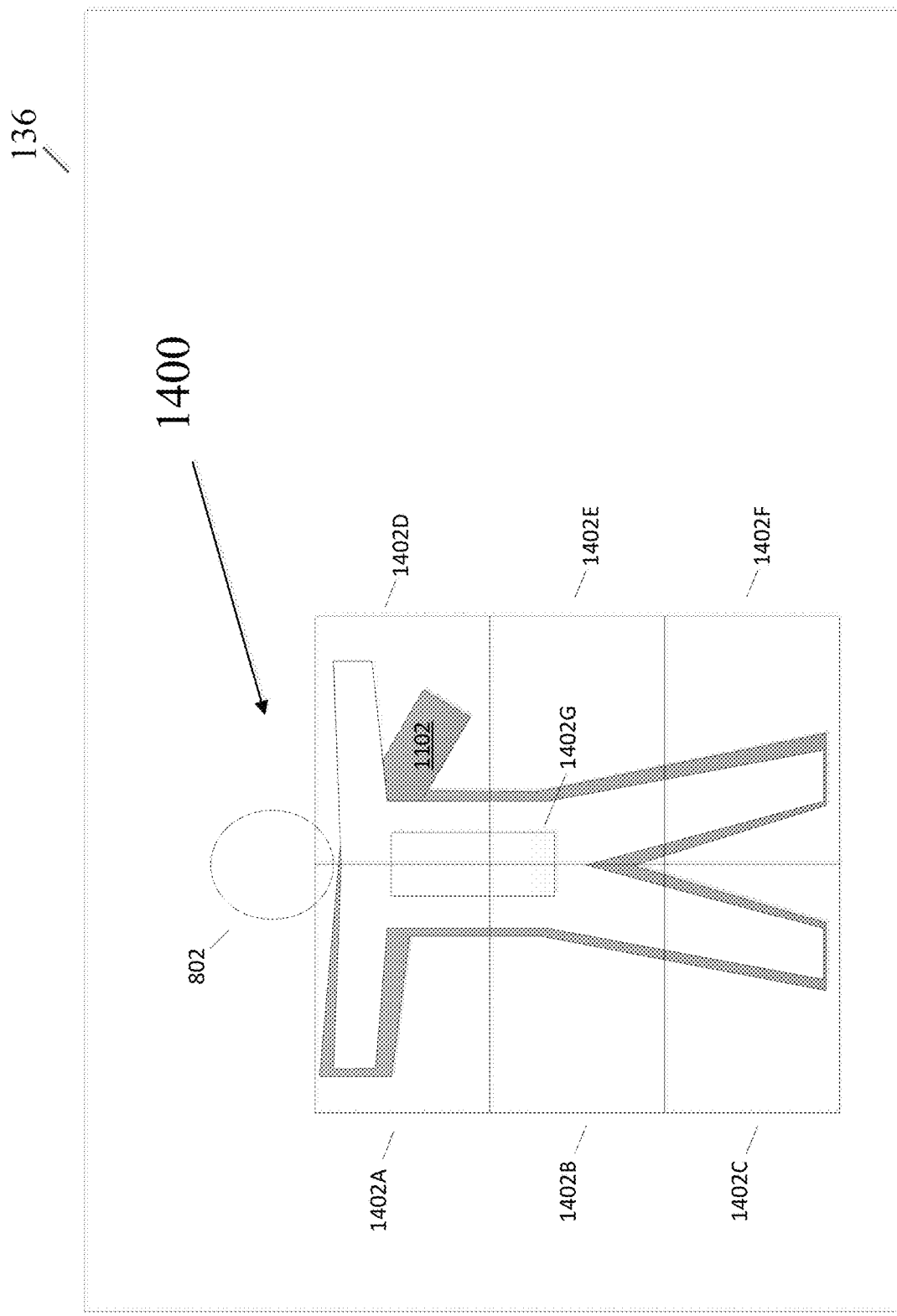
FIG. 14 illustrates an example display of image subsections for determining an amount of overlap between a user avatar and a virtual shadow in accordance with example embodiments.

Further aspects relate to systems and methods for determining overlap. In one embodiment, computer 102 (or any other electronic device) may divide an image from captured video into subsections to identify body parts that may be performing an incorrect movement, as shown in FIG. 14. In other embodiments, the sub-sections may be the similar to the regions discussed in relation to FIG. 5.

Looking to FIG. 14, computer 102 may divide sensed data, represented by image 1400, into unique subsections 1402 and may determine the amount of overlap between the shadow 1102 and the user avatar 802 in each subsection. In one embodiment, one or more subsections 1402 may correspond to quadrants, such as the quadrants illustrated in FIG. 5. In an example, FIG. 14 shows six different subsections 1402A-F; however, any desired number may be used. Computer 102 may compare the overlap to identify a subsection having a lowest percentage of overlap (e.g., subsection 1402D in FIG. 14). Computer 102 also may identify one or more subsections having a percentage overlap below a predetermined amount (e.g., less than 60%).

In other examples, computer 102 may determine an amount of overlap by processing the infrared data and/or the sensor data to determine locations, of a user's body parts (such as for example, one or more of locations 402a-m), and comparing the identified locations to desired locations. Computer 102 may define overlap zones that compare the amount of distance between a desired body part location and an actual location. For example, a good form zone may be within a first distance from a desired location (e.g., elbow is within 2 inches from desired location) or vary by no more than a certain percentage (e.g., 5%) from the desired location. An acceptable form zone may be within a second distance range of a desired location (e.g., elbow is within 2-4 inches from desired location) or where a body part differs by no more than a certain percentage (e.g., 15%) from the desired location. An unacceptable form zone may be more than a certain distance away from a desired location and/or where a body part differs by more than a certain percentage (e.g., more than 15%) from a desired location. Any number of zones may be defined.

e. Corrections

As part of the overlap determinations and/or other criteria, system 100 may cause the display 136 to present a recommended correction to the user's form. This may be performed whether there is an indication of either an acceptable form zone or an unacceptable form zone. With reference to FIG. 10B, the displayed instruction 1006 may be provided to prompt the user to straighten their knees. Computer 102 may also cause the displayed video of the user avatar 802 to flash a color, to highlight a particular body part in color (e.g., highlight hip region, elbow, etc. see 1004 of FIG. 10), to sound a tone or provide an audible instruction (e.g., straighten your back), to zoom in on or enlarge video of a body part or region of a user's body that has poor form, display a chart illustrating a difference between measured and desired form (e.g., angle between upper arm and form is 25% greater than desired), or other manners to audibly or visually inform the user of the problem. Although the correction is shown as part of avatar 802, other embodiments may show corrections as part of a shadow.

System 100 may provide feedback to correct one problem at a time, and certain problems may take priority over others. Certain exercises or movements may place a user at risk for injury if not performed properly. Improper form that may result in injury may be of the highest priority, and from there other improper body part locations may be prioritized to assist the user in obtaining the full benefit of the exercise.

When in the unacceptable form zone, computer 102 may provide feedback identifying misplaced body parts attempting to improve the user's form to move into the acceptable form zone. Once in the acceptable form zone, computer 102 may provide feedback identifying misplaced body parts attempting to improve the user's form to move into the good form zone. If the user's form continues to be in the unacceptable form zone after a predetermined number of repetitions, computer 102 may stop the exercise or routine. In certain embodiments, system 100 may inform the user of the error and/or demonstrate the exercise again. Computer 102 may also change the exercise to an easier one or may adapt the repetitions based on a user's execution. As the user's form improves over time, computer 102 may shift from providing corrective feedback (e.g., instruction and correction) to providing motivation.

Figure 15:
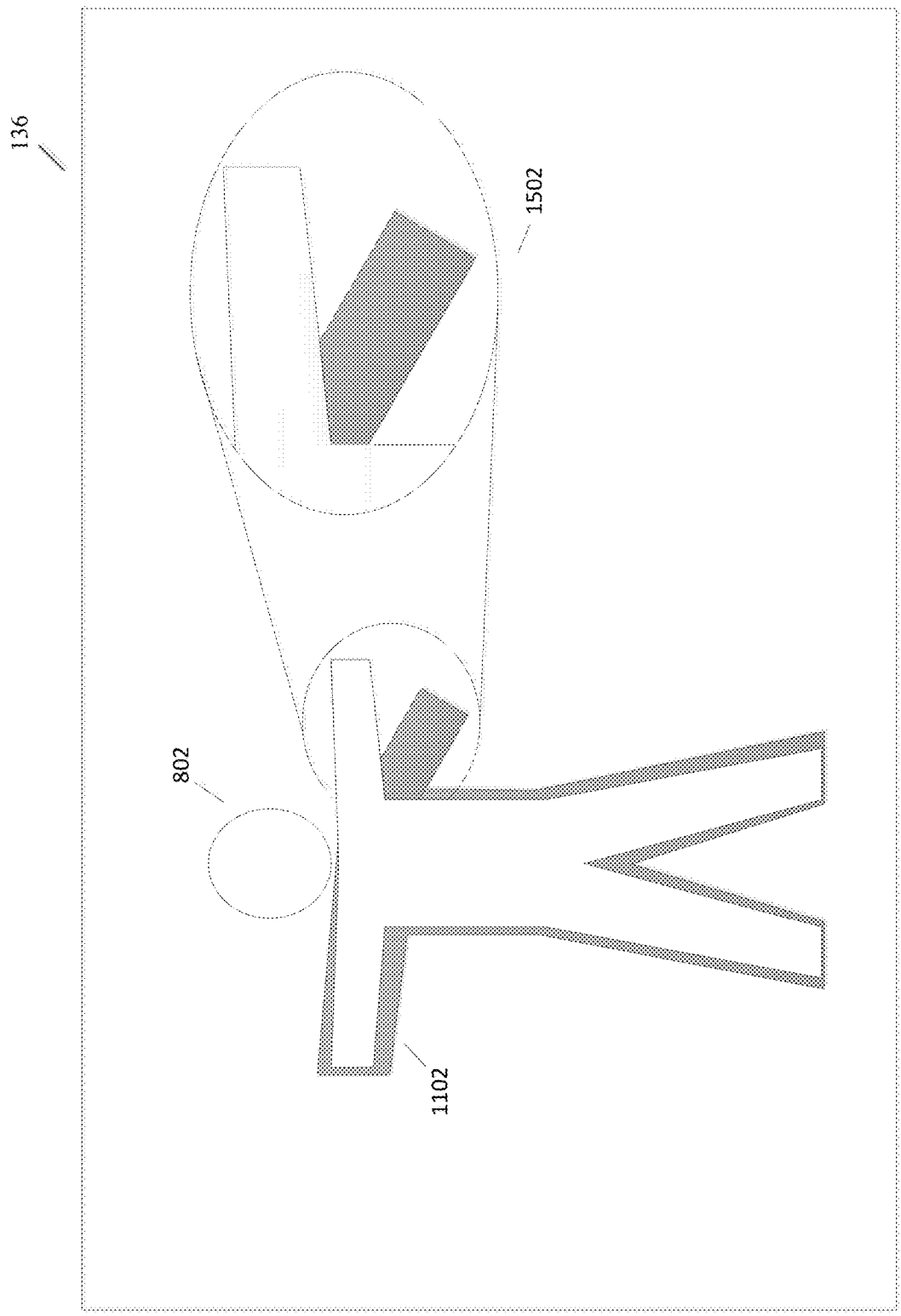
FIG. 15 illustrates an example display of a user avatar having a magnified inset view providing feedback on improper form while performing an exercise in accordance with example embodiments.

FIG. 15 illustrates an example display of a user avatar having a magnified inset view providing feedback on improper form while performing athletic movements in accordance with example embodiments. For the one or more body parts identified as having improper form (e.g., such as an identified subsection 1402 shown in FIG. 14 having insufficient overlap with a virtual shadow 1102 and/or or falling within an unacceptable form zone), system 100 may provide one or more inset magnified views. For example, magnified view 1502 of FIG. 15 shows a body portion of the user avatar 802 that does not coincide (such as within a minimum threshold) with the virtual shadow 1102. As seen in FIG. 15, an arm of the user avatar 802 is not located at the same position as a corresponding arm of the shadow 1102. This portion of the user avatar 802 is presented in a magnified inset view 1502. The magnified inset view 1502 may also highlight the user avatar 802 in a first color (e.g., red) to emphasize the problem.

In another aspect, computer 102 may provide a replay feedback mode permitting a user to review their performance of an exercise. In one example, computer 102 may determine instances in the video when overlap between the user avatar 802 and shadow 1102 decreased below a certain threshold. For example, computer 102 may process subsections 1402 of each image, or at least some of the images, of the video to identify a subsection where overlap between the user avatar 802 and shadow 1102 decreased below a threshold. System 100 may identify and store a predetermined number of preceding images from the video corresponding to the identified subsection 1402 and continue storing images from the video until the overlap between the user avatar 802 and shadow 1102 increases above the threshold. The stored images may be referred to as a variance sequence.

System 100 may provide the user with feedback on the number of variance sequences collected during athletic movements, and one or more body parts involved causing the variance. Display 136 may display each of the variance sequences to provide the user with feedback on their form. System 100 may also present the virtual trainer avatar 802 to provide an example of proper form with an enlarged view of the problem area and/or recommend remedial exercises and/or drills to aid the user in having proper form.

Figure 16B:
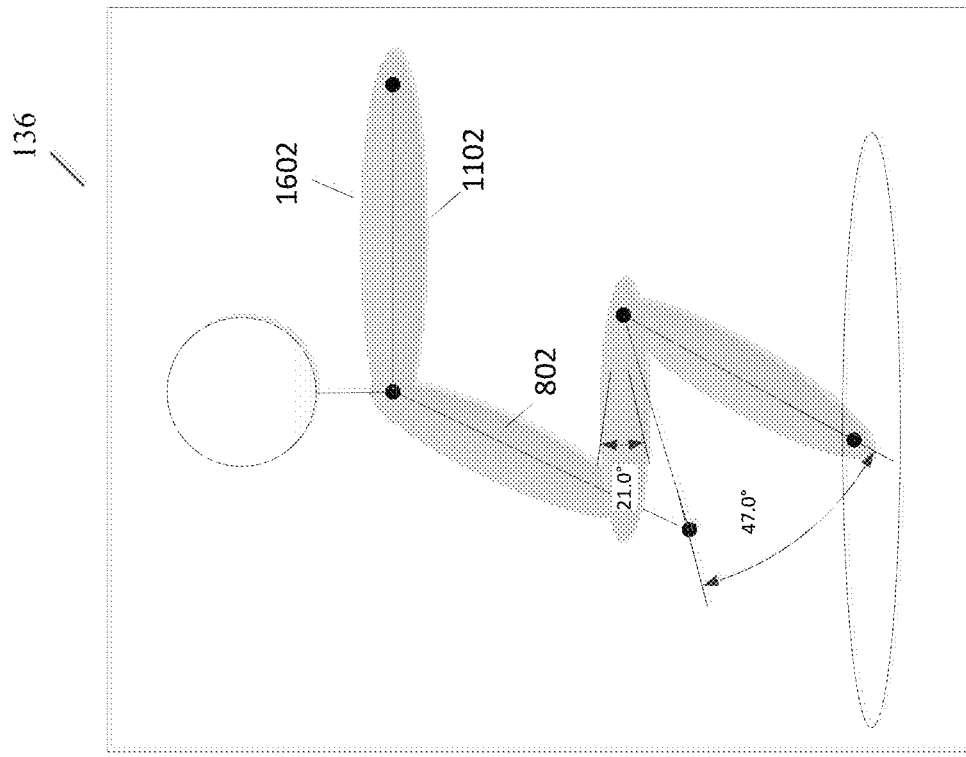
FIGS. 16A-16B illustrate example displays for depicting a user avatar relative to a virtual shadow for detecting improper form and providing feedback to a user in accordance with example embodiments.
Figure 16A:
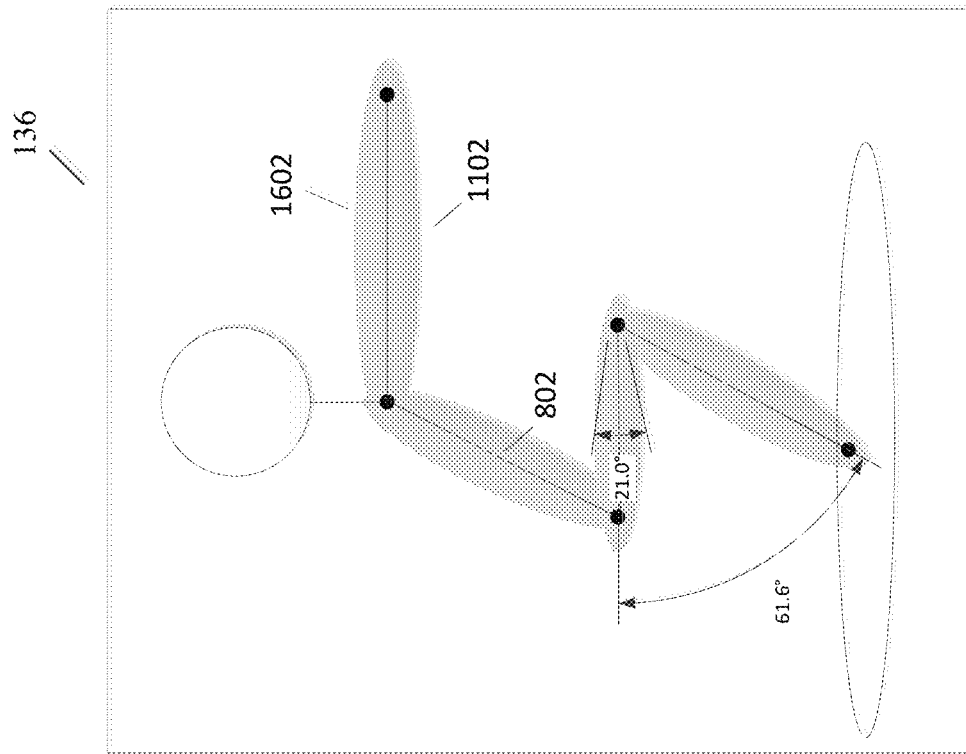

FIGS. 16A-B illustrate example displays for depicting a user avatar relative to a virtual shadow for detecting improper form and providing feedback to a user in accordance with example embodiments. In FIG. 16A, a user avatar 802 is represented by lines positioned within a shadow 1102. System 100 may monitor the user's form and look for certain angles between a user's body parts, as well as determining whether the user avatar 802 remains within the shadow 1102. For example, the system 100 may monitor an angle between the thigh and shin of the user avatar 802, as well as an angle between a user's torso and thighs. In an example, a desired angle between a user's thigh and shin may be 61.6°, and acceptable form may be within a range of 21° of the desired angle (e.g., between 50.5° and 72.1°). In FIG. 16B, an angle between the thigh and shin of the user avatar 802 may fall outside of the desired range (e.g., 47°). To emphasize that the user (represented by avatar 802) has improper form, the avatar 802 may be displayed as not being completely within the shadow 1102. As seen in FIG. 16B, the thigh of the user avatar 802 is outside of the thigh of the shadow 1102. For example, shadow may be defined with an area having an outer perimeter, such as perimeter 1602. Although perimeter 1602 is shown as a single perimeter, those skilled in the art with the benefit of this disclosure will understand that shadow 1102 may be comprised of multiple sections or regions, each with their own respective perimeter. Also, the problem area may be highlighted in the display 136 with an instruction to improve the user's form. For example, the display 136 may present an instruction that instructs the user to maintain their thighs parallel to the ground at the lowest point of a squat. Data received from multiple sensors, which may be variously disposed (including on the user) may be utilized in these and other determinations.

f. Skill Level Determinations

With reference again to FIG. 13A, virtual shadow 1102 may also be used to signify a skill level of the user. In one example, system 100 may adjust a size of the virtual shadow 1102 based on a user's ability to maintain proper form. Computer 102 may determine whether a user is able to use proper form based on their ability to maintain the user avatar 802 within the virtual shadow 1102 while performing an exercise. The size of the shadow 1102 may correspond to a skill level of the user in performing an exercise. For example, in certain implementations, a novice user may begin with a larger virtual shadow. The size of the shadow (or portions thereof) may be reduced until it substantially conforms to a virtual size of the user's body.

Initially, system 100 may instruct the user 124 to perform a series of exercises to assess a user's form for each exercise. For example, either continuously or at a certain discrete points within an exercise, system 100 may compare a location of various body parts of the user avatar 802 to the shadow 1102. For example, the discrete points may correspond to certain positions within an exercise where a user's form may be important to ensure that a particular a muscle or muscle group is being worked and/or to prevent or reduce the likelihood of a user injuring him or herself. In one example, computer 102 may determine an amount of overlap between the user avatar 802 and the shadow 1102. In an example, computer 102 may also define multiple shadows, where a first shadow is a beginner shadow, a second shadow is an intermediate shadow, and a third shadow is an expert shadow. Of course, any number of shadows may be defined.

System 100 may compare a user's form to each of the three (or more) shadows, for example, by determining an amount of overlap with each. In one example, at least some of the shadows may be associated with a threshold amount of overlap. The overlap threshold amount may represent a minimum amount of overlap with the shadow to have reached the skill level for that shadow. For example, the novice shadow may not be associated with a threshold, the intermediate shadow may be associated with an 85% overlap threshold, and the expert shadow may be associated with a 90% overlap threshold. Thresholds may be in relation to the entire shadow or with respect to certain regions of it.

To determine that a user has reached a certain skill level, system 100 may determine if the amount of overlap between the user avatar 802 and a particular shadow exceeds the overlap threshold for that shadow. In an example, system 100 may take calculate the amount of overlap of the user avatar 802 with each of the shadows at certain times during an exercise or series of athletic movements, and average the overlap amounts. System 100 may compare the average to each of the thresholds and assign the user 124 a particular one of the shadows based on their skill level. For example, computer 102 may determine that a user avatar 802 has an average overlap amount of 95% with the novice shadow, an average overlap amount of 85% with the intermediate shadow, and a 60% average overlap amount with the expert shadow.

Using the example thresholds above, system 100 may classify the user 124 as having an intermediate skill level and display the intermediate shadow when the user subsequently performs that exercise. Computer 102 may monitor the user over time and inform the user when their form has improved so that they can exercise with a next higher skill level shadow. System 100 may also move the user to a next lower skill level shadow if their form declines. Computer 102 may communicate a user's shadow size and overlap percentage for that shadow to the server 134. For example, the server 134 may provide a social networking website and may rank users based on their shadow size.

5. Overlap Score Determinations

Further embodiments may include generating a feedback score based on the amount of overlap (see, e.g., block 312 of FIG. 3). In an example, system 100 may generate a feedback score based on how well the user controlled the user avatar 802 to correspond to the virtual shadow 1102. For instance, system 100 may provide a scoring algorithm for indicating how well the user controlled the user avatar 802 to correspond to the virtual shadow 1102. A user's score may be uploaded to a social network or website, such as through server 134, and utilized in the ranking of users relative to one another or a standard.

System 100 may monitor a location of individual body parts of the user or groups of body parts, and assign a location score to each body part or body part group based on whether each is in the correct location. With reference to FIG. 8, for example, computer 102 may determine an angle between a straight line across a user's hips and form guidance information 702. Computer 102 may assign an angle score based on the angle between the line of current form information 804 and the line of form guidance information 702. A smaller angle may correspond to a higher score. In another example, with reference to FIG. 16B, system 100 may assign an angle score based on relative positions of body parts. For example, computer 102 may assign an angle score based on comparing an angle between a thigh and shin of a user to a desired angle. Rotation of a first body part or region with respect to a second body part or region may be determined. In one embodiment, one or more sensors may be positioned or configured to detect the orientation, position, and/or distance of the user 124 with respect to another object. For example, a reference point in the user's environment or on the user may be utilized to determine relative aspects of the user, including location, movements, rotation, orientation, and combinations thereof.

In another example, with reference to FIGS. 10A-10B, system 100 may assign a target score if a user is able to place a body part within a virtual target 1002 at one or more time intervals. In yet another example, system 100 may assign an overlap score based on the amount of overlap of a user avatar 802 relative to a shadow 1102.

In certain embodiments, system 100 may determine a workout score as a sum of the scores. The scores assigned may vary by type of exercise, and some scores may be weighted more heavily than others. For example, a workout score may be a weighted sum of one or more angle scores, one or more virtual target scores, and one or more overlap scores. Scores may also be negative. In an example, computer 102 may determine a sum of two angle scores (e.g., between torso and thigh, and between thigh and shin), a virtual target score, and an overlap score. Computer 102 may communicate the total score to the server 134, which may rank the user relative to other users based on their form during a particular movement or series of movements.

6. Body Systems Feedback

Figure 17:
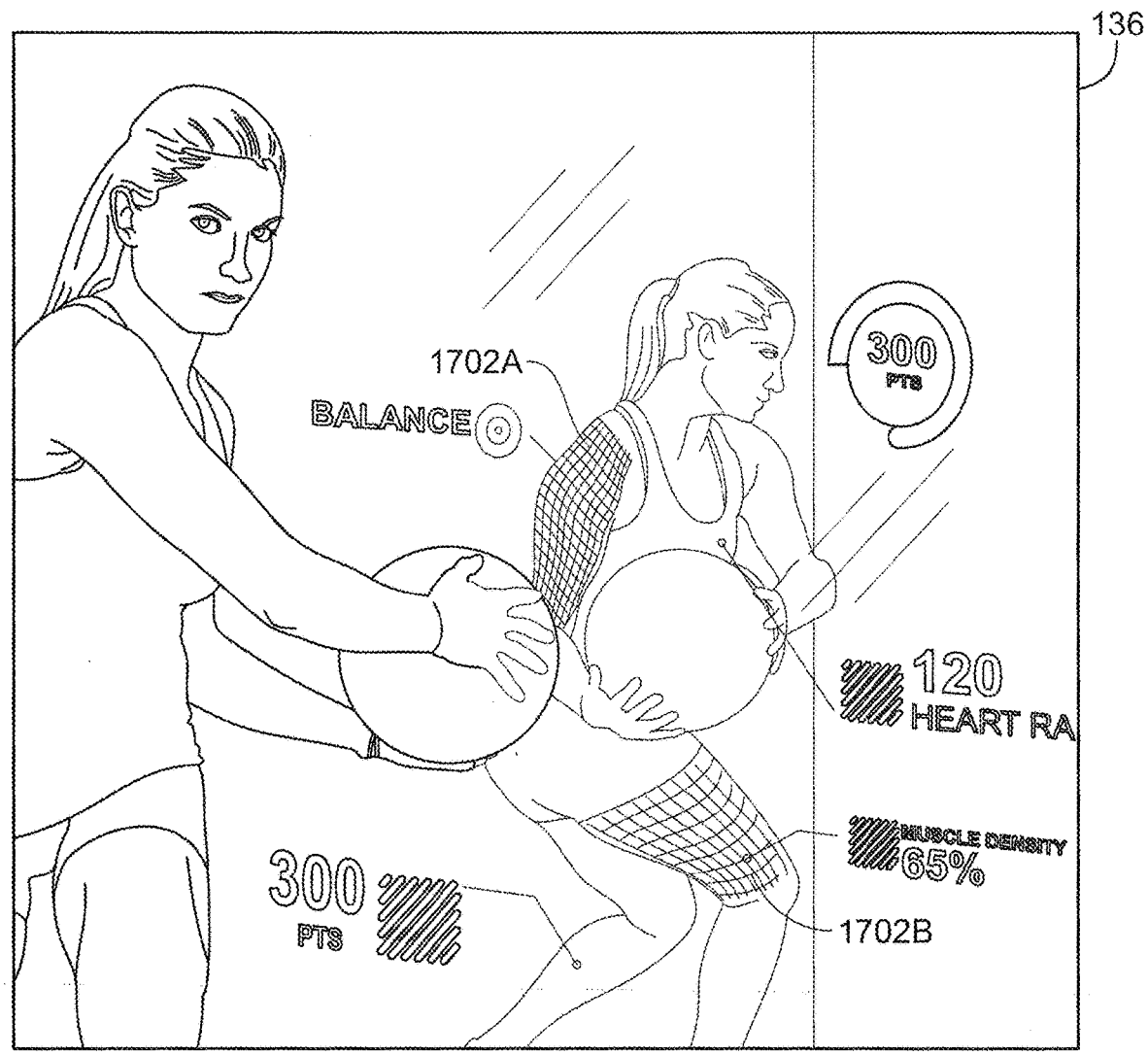
FIG. 17 illustrates an example of onion skinning on an image of a user in accordance with example embodiments.

In additional examples, the display 136 may inform the user of body systems targeted during athletic activities, such as muscle groups targeted during an exercise. FIG. 17 illustrates an example display providing a user with feedback on muscles being developed by an exercise in accordance with example embodiments. In one embodiment, system 100 may process an image of the user 124 and cause the display 136 to present a grid 1702A/1702B on one or more muscles being developed by an exercise. As seen in FIG. 17, a grid 1702A is displayed proximate to a user's shoulder and arm, and a grid 1702B is displayed proximate to a user's hamstring. Displaying a grid on a user's muscle or muscle group may be referred to as "onion-skinning." Onion skinning may be used to focus a user's attention on a particular system or region, such as a muscle or muscle group worked during an exercise. System 100 may also cause the display 136 to present onion skinning on the virtual trainer avatar 602 during demonstration of an exercise. After or during a workout, the user 124 may select the onion skinned location using a computer mouse or other input device, by making a motion in front of the image capturing device 126, or by a voice command to instruct computer 102, to peel back the avatar's skin to display the muscle working during the exercise.

FIG. 18 illustrates an example flow diagram of a method for providing virtual competition in a virtual environment, such as between multiple virtual avatars, in accordance with one or more example embodiments. Various methods may be implemented by a computer, such as, for example, computer 102, device 138, 140, 142 and/or 144, and/or other apparatuses. The blocks shown in FIG. 18 may be rearranged, some blocks may be removed, additional blocks may be added, each block may be repeated one or more times, and the flow diagram may be repeated one or more times. The flow diagram may begin at block 1802.

In block 1802, one or more embodiments may include prompting a first user, such as user 124, to perform at least one exercise during a workout session. In an example, computer 102 may prompt a user to perform one or more exercises during a workout session. A workout session may include a predetermined number of exercises (e.g., pushups, squats, lunges, etc.) where computer 102 prompts the user to perform a predetermined number of repetitions of each exercise. A workout session may also involve a single athletic activity (e.g., run 10 miles).

Figure 19:
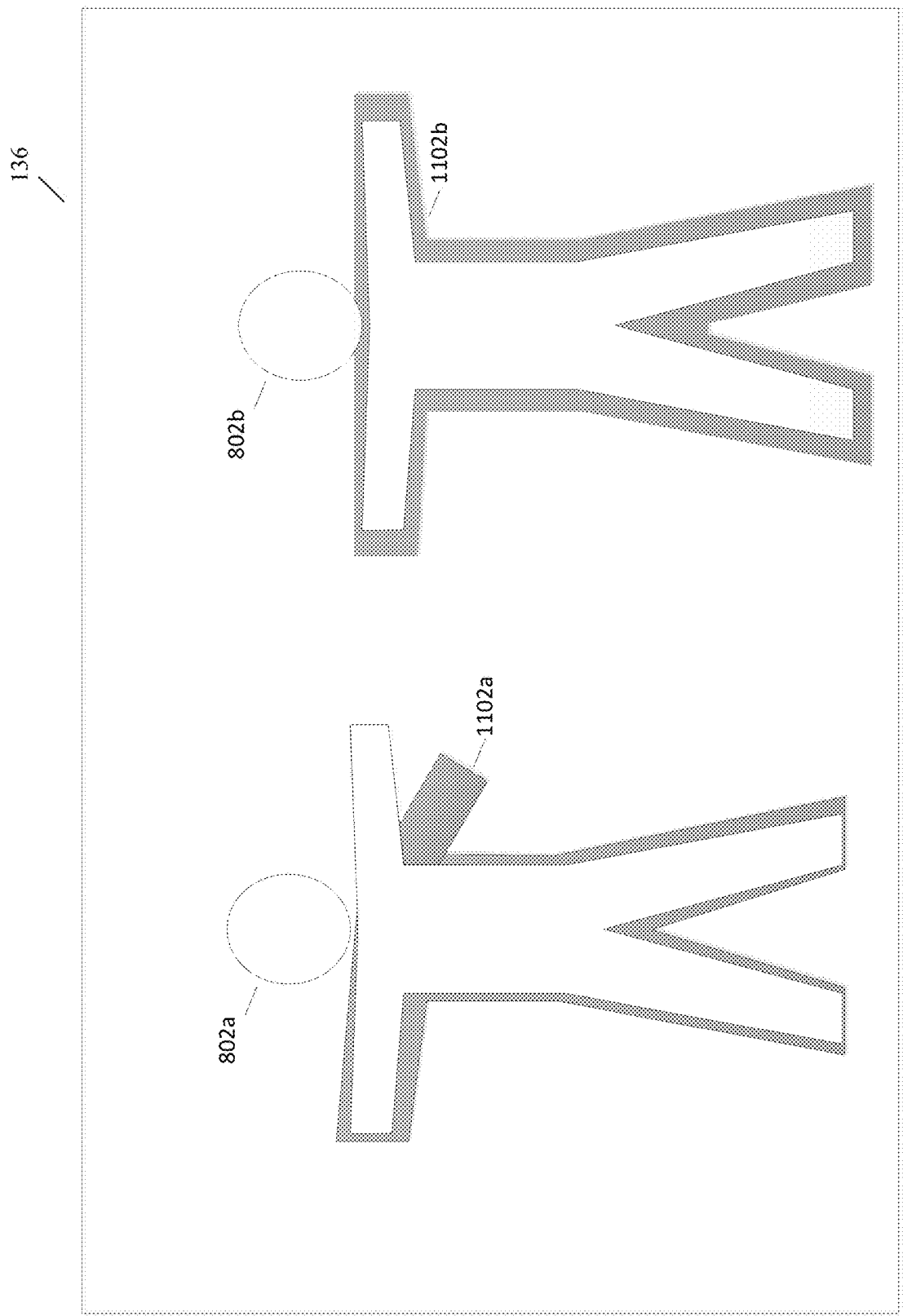
FIG. 19 illustrates multiple avatars, each having a shadow, competing in a virtual environment, in accordance with one or more example embodiments.

As part of the workout session, the user 124 may compete against their previous performance of the workout session or another user. For example, computer 102 may display multiple avatars, where a first user avatar corresponds to their current performance, and a second user avatar corresponds to a previous performance of the workout session. FIG. 19 illustrates an example display of multiple avatars 802a-b competing against one another in a virtual environment.

In another example, a second of the user avatars 802b may be based on data obtained from monitoring a second user (e.g., not user 124) during a workout session. The data may be received from a remote location (e.g., communicated via network 132) or from the same location as the first user 124. In an example, the second user may complete a particular workout session where their computer monitors the second user's performance, and cause their computer to send a challenge to computer 102 challenging the first user to beat their performance. The challenge may include data of the second user performing the particular workout session. In a further example, both users may perform a workout session at the same time, where respective computers 102 may monitor each user's performance, and exchange data with the other user's computer via network 132 so that each computer can cause display of the other's avatar in a virtual competition.

In block 1804, one or more embodiments may include monitoring with a monitoring device the first user performing the at least one exercise. As discussed above, various monitoring devices, such as, for example, sensors 128, 138, 140, 142, and 144 and/or camera 126, may capture data of the user performing one or more exercises.

In block 1806, one or more embodiments may include generating a first virtual avatar of the first user based on data captured by the monitoring device. As explained throughout this disclosure, multiple sensors may be utilized, either in combination or alone, to monitor data. In one embodiment, computer 102 may generate a virtual avatar 802a of the user based on data captured by one or more of sensors 128, 138, 140, 142, 144 and/or camera 126

In block 1808, one or more embodiments may include generating a first virtual shadow for the first virtual avatar that is based on attributes relating to the first user. As discussed above, computer 102 may generate a virtual shadow 1102a. For example, computer 102 may generate a virtual shadow 1102a having a particular size based on the skill level of the user.

In block 1810, one or more embodiments may include receiving second user data corresponding to a second user for generating a second virtual avatar and a second virtual shadow. In certain implementations, the second virtual avatar is based on monitoring of the second user performing the at least one exercise and the second virtual shadow is based on attributes relating to the second user. In an example, system 100 may receive data captured by monitoring a second user performing the same exercises in the workout session. The received data may also include information on a virtual shadow of the second user. The second user data may be based on simultaneous performance of the workout sessions by the users, or may be based on a previously completed workout session.

In block 1812, one or more embodiments may include displaying simultaneously on a display device the first and second virtual avatars 802a-b and the first and second virtual shadows 1002a-b. In an example, computer 102 may cause display 136 to simultaneously display a virtual avatar 802a-b corresponding to each of the users. Display 136 may also display a virtual shadow 1102a-b for each avatar. Computer 102 may synchronize the start of the workout session to permit the avatars 802a-b to compete in a virtual environment. In an example, the competition may be of a footrace, a race where user's movement causes a vehicle to move, weightlifting, jumping, or other type (or combinations) of athletic competition. The virtual environment presented by display 136 may correspond to the activity being performed. For example, the virtual environment may be a track for a footrace, a gym for a weightlifting session, etc.

To provide for competition between the users, computer 102 may score how well each of the users is able to maintain their virtual avatar 802a-b within their shadow 1102a-b during the workout session, and may display the scores at the end of the session. For instance, computer 102 may generate a first score for a first user based on movement of the first virtual avatar 802a relative to the first virtual shadow 1102a during the workout session and a second score for a second user based on movement of the second virtual avatar 802b relative to the second virtual shadow 1102b during the workout session. Users may receive points by maintaining their user avatar 802 within its shadow 1102, and may lose points when falling outside of the shadow 1102.

The size of each shadow 1102a-b may correspond to a skill level of a user. For example, a higher skill level may result in a smaller shadow 1102 that is tailored to the shape of the user avatar 802, thus allowing a user less margin for error to maintain their avatar 802 within the virtual shadow 1102. Conversely, a lower skill level may correspond to a larger shadow 1102 permitting a user a greater margin of error. Computer 102 may also apply a handicap to the first virtual shadow 1102a or the second virtual shadow 1102b based on skill level of the first user relative to skill level of the second user, so that competitors can be challenged regardless of each user's actual skill level. To implement the handicapping, computer 102 may, for example, adjust a size of the first virtual shadow 1102a or the second virtual shadow 1102b.

At the completion of the workout session, computer 102 may determine a score for each user, as well as who had a better score (e.g., winner) during the workout session. Computer 102 may also display one or more performance metrics for each of the users for comparison based on the type of exercises being performed. For example, computer 102 may display an aggregate total (e.g., total number of pushups completed), highest attribute (e.g., fastest speed, greatest distance, etc.), average metric (e.g., average speed), or other athletic performance information. With reference to FIG. 18, the method may end or return to any of the preceding blocks.

CONCLUSION

Providing an activity environment having one or more of the features described herein may provide a user with an immersive experience that will encourage and motivate the user to engage in athletic activities and improve his or her fitness. Users may further communicate through social communities and challenge one another to reach various levels of fitness, and to view their fitness level and activity.

Aspects of the embodiments have been described in terms of illustrative embodiments thereof. Numerous other embodiments, modifications and variations within the scope and spirit of the appended claims will occur to persons of ordinary skill in the art from a review of this disclosure. For example, one of ordinary skill in the art will appreciate that the steps illustrated in the illustrative figures may be performed in other than the recited order, and that one or more steps illustrated may be optional in accordance with aspects of the embodiments.

What is claimed is:

1. A computer-implemented method comprising:
providing instructions to a user to perform an athletic movement;
monitoring with at least a first accelerometer sensor the user performing the athletic movement;
generating a virtual avatar of the user during the user's performance of the athletic movement, the virtual avatar having a contiguous area shaped like a human subject, wherein the contiguous area comprises a plurality of appendage-like sub-areas representing appendages of the human subject;
displaying on a display device the virtual avatar overlaid relative to a virtual target, the virtual target comprising a ring shape through which the virtual avatar can extend a selected one or more of the plurality of appendage-like sub-areas representing appendages of the human subject, wherein the virtual target is colored based upon a performance threshold for the user, and wherein the virtual target is configured to illustrate a proper form of the athletic movement, such that if the user performing the proper form of the athletic movement, then a portion of the contiguous area is within the virtual target;
determining, by a processor, an amount of overlap between the virtual avatar and the virtual target; and
generating in real time, a feedback score based on, at least in part, the amount of overlap.

2. The method of claim 1, further comprising:
generating the virtual target, wherein a size of the virtual target is based, at least in part, according to a skill level determined for the user.

3. The method of claim 1, further comprising:
determining a skill level for the user based on an amount of overlap between the virtual avatar and the virtual target.

4. The method of claim 1, wherein the monitoring of the user comprises receiving a plurality of images from an image capture device, and wherein the method further comprises:
processing subsections of at least one image from the plurality of images to determine an amount of overlap between the virtual avatar and the virtual target within each of the subsections.

5. The method of claim 4, further comprising:
identifying a subsection in which the amount of overlap is less than a predetermined threshold.

6. The method of claim 5, further comprising: displaying a magnification of the identified subsection.

7. The method of claim 1, further comprising:
communicating the feedback score via a network; and
ranking the user relative to at least one other user who performed the athletic movement.

8. The method of claim 1, further comprising:
determining a virtual target score based on a measuring whether the user moved a body part to coincide with the virtual target, wherein the feedback score is based, at least in part, on the virtual target score.

9. The method of claim 1, further comprising:
determining an angle score based on a comparing an angle between two body parts of the user during performance of the athletic movement and a desired angle between the two body parts during the athletic movement, wherein the feedback score is based on the angle score.

10. The method of claim 1, further comprising:
determining an overlap score based on an amount of overlap between the virtual avatar and the virtual target, wherein the feedback score is based on the overlap score.

11. The method of claim 1, wherein the feedback score is based on a weighted sum of an angle score, a virtual target score, and an overlap score.

12. A non-transitory computer-readable medium comprising computer-executable instructions that, when executed, perform a method comprising:
provide instructions to a user to perform an athletic movement;
monitoring with at least a first accelerometer sensor the user performing the athletic movement;
generating a virtual avatar of the user during the user's performance of the athletic movement, the virtual avatar having a contiguous area shaped like a human subject, wherein the contiguous area comprises a plurality of appendage-like sub-areas representing appendages of the human subject;
generating a virtual target, the virtual target comprising a ring shape through which the virtual avatar can extend a selected one or more of the plurality of appendage-like sub-areas representing appendages of the human subject, wherein the virtual target is colored based upon a performance threshold for the user, and wherein the virtual target is configured to illustrate a proper form of the user's athletic movement such that if the user performs the proper form of the athletic movement, then a portion of the contiguous area is entirely within the virtual target;
displaying on a display device the virtual avatar overlaid relative to the virtual target;
determining, by a processor, an amount of overlap between the virtual avatar and the virtual target; and
generating in real time a feedback score based on the amount of overlap.

13. The non-transitory computer readable medium of claim 12, wherein the computer-readable medium further comprises instructions that when executed, perform the method comprising:
determining a skill level for the user based on an amount of overlap between the virtual avatar and each of a plurality of virtual targets, wherein each of the virtual targets is associated with a threshold.

14. The non-transitory computer readable medium of claim 12, wherein the monitoring of the user comprises receiving a plurality of images from an image capture device, and wherein the method further comprises:
processing subsections of at least one image from the plurality of images to determine an amount of overlap between the virtual avatar and the virtual target within each of the subsections.

15. The non-transitory computer readable medium of claim 14, wherein the computer-readable medium further comprises instructions that when executed, perform the method comprising:
identifying a subsection in which the amount of overlap is less than a predetermined threshold; and
displaying a magnification of the identified subsection.

16. The non-transitory computer readable medium of claim 12, wherein the computer-readable medium further comprises instructions that when executed, perform the method comprising:
determining an angle score based on a comparing an angle between two body parts of the user during performance of the athletic movement and a desired angle between the two body parts during the athletic movement, wherein the feedback score is based on the angle score.

17. An apparatus comprising:
at least one processor; and
at least one non-transitory memory storing instructions that, when executed, cause the apparatus at least to perform:
providing instructions to a user to perform an athletic movement;
monitoring with at least a first accelerometer sensor the user performing the athletic movement;
generating a virtual avatar of the user during the user's performance of the athletic movement, the virtual avatar having a contiguous area shaped like a human subject, wherein the contiguous area comprises a plurality of appendage-like sub-areas representing appendages of the human subject;
displaying on a display device the virtual avatar overlaid relative to a virtual target, the virtual target comprising a ring shape through which the virtual avatar can extend a selected one or more of the plurality of appendage-like sub-areas representing appendages of the human subject, wherein the virtual target is colored based upon a performance threshold for the user, and wherein the virtual target illustrates a proper form of the athletic movement, such that if the user performing the proper form of the athletic movement, then the contiguous area is entirely within the virtual target;
determining, by a processor, an amount of overlap between the virtual avatar and the virtual target; and
generating in real time a feedback score based on the amount of overlap.

18. The apparatus of claim 17, wherein the instructions, when executed, cause the apparatus to determine a skill level based on an amount of overlap between the virtual avatar and each of a plurality of virtual targets, wherein each of the virtual targets is associated with a threshold.

19. The apparatus of claim 17, wherein the monitoring of the user comprises recording of video of the user, and wherein the instructions, when executed, cause the apparatus to:
process subsections of at least one image from a plurality of images to determine an amount of overlap between the virtual avatar and the virtual target within each of the subsections;
identifying a subsection in which the amount of overlap is less than a predetermined threshold; and
displaying a magnification of the identified subsection.

20. The apparatus of claim 17, wherein the instructions, when executed, cause the apparatus to:
determine a virtual target score based on a measuring whether the user moved a body part to coincide with the virtual target;
determine an angle score based on a comparing an angle between two body parts of the user and a desired angle between the two body parts; and
determine an overlap score based on determining an amount of overlap between the virtual avatar and the virtual target, wherein the feedback score is based on a weighted sum of the angle score, the virtual target score, and the overlap score.

* * * * *